United States Patent
Weibel

(10) Patent No.: US 9,650,187 B2
(45) Date of Patent: May 16, 2017

(54) DEVICE FOR RECEIVING AND DISPENSING A FLUID

(75) Inventor: Ludwig Daniel Weibel, Waldstatt (CH)

(73) Assignee: Weibel CDS AG, Waldstatt (CH)

( * ) Notice: Subject to any disclaimer, the term of this patent is extended or adjusted under 35 U.S.C. 154(b) by 518 days.

(21) Appl. No.: 14/126,085

(22) PCT Filed: Jun. 19, 2012

(86) PCT No.: PCT/EP2012/061634
§ 371 (c)(1),
(2), (4) Date: Dec. 13, 2013

(87) PCT Pub. No.: WO2012/175465
PCT Pub. Date: Dec. 27, 2012

(65) Prior Publication Data
US 2014/0131389 A1 May 15, 2014

(30) Foreign Application Priority Data

Jun. 21, 2011 (EP) .................................... 11170663

(51) Int. Cl.
*B65D 47/20* (2006.01)
*B65D 47/12* (2006.01)
(Continued)

(52) U.S. Cl.
CPC .......... *B65D 47/205* (2013.01); *A61J 1/1481* (2015.05); *A61M 5/148* (2013.01); *A61M 5/282* (2013.01);
(Continued)

(58) Field of Classification Search
CPC .. B65D 47/205; B65D 83/0055; B65D 35/28; F16K 7/17
(Continued)

(56) References Cited

U.S. PATENT DOCUMENTS 3,114,369 A 12/1963 Hall
5,305,783 A 4/1994 Debush
(Continued)

FOREIGN PATENT DOCUMENTS

| DE | 3224656 | 4/1983 |
|---|---|---|
| DE | 202007008646 | 12/2007 |
| WO | 02/079679 | 10/2002 |

*Primary Examiner* — Timothy P Kelly
(74) *Attorney, Agent, or Firm* — Davis & Bujold PLLC; Michael J. Bujold

(57) ABSTRACT

The invention relates to a device (1) for receiving or dispensing a fluid (39), preferably containing a pharmaceutical, comprising a container that can be collapsed at least in some regions and a closure piece (2). The closure piece (2) comprises a dispensing channel (18) that fluidically connects a dispensing opening (2.1) to a removal opening (21), wherein a dispensing section (18.1) of the dispensing channel (18) communicates with the dispensing opening (2.1) and a removal section (18.2) of the dispensing channel (18) communicates with the removal opening (21). The dispensing channel (18) comprises a valve device (23) having two valve openings (22, 25), which are arranged next to one another on a valve surface (6.1). A first valve opening (25) of said valve device communicates with the dispensing opening (2.1) via the dispensing section (18.1) of the dispensing channel (18) and a second valve opening (22) communicates with the removal opening (21) via the removal section (18.2) of the dispensing channel (18), wherein a continuous flexible diaphragm (27) is provided, which in a closed position of the valve device (23) is seated against of the valve surface (6.1) and can be lifted in some regions and thus seals the valve openings (22, 25) with respect to one another in a fluid-tight manner.

13 Claims, 10 Drawing Sheets

(51) Int. Cl.
  *A61M 5/148* (2006.01)
  *A61M 5/28* (2006.01)
  *A61M 5/34* (2006.01)
  *A61J 1/14* (2006.01)
  *A61M 39/10* (2006.01)
  *A61M 5/31* (2006.01)
  *A61J 1/20* (2006.01)
  *A61J 1/10* (2006.01)

(52) U.S. Cl.
  CPC .............. *A61M 5/345* (2013.01); *B65D 47/12* (2013.01); *A61J 1/10* (2013.01); *A61J 1/2037* (2015.05); *A61M 5/347* (2013.01); *A61M 2005/3103* (2013.01); *A61M 2005/3118* (2013.01); *A61M 2005/3128* (2013.01); *A61M 2039/1072* (2013.01)

(58) Field of Classification Search
  USPC .............. 141/2; 222/209, 212, 213, 96, 494; 251/61, 61.1
  See application file for complete search history.

(56) References Cited

U.S. PATENT DOCUMENTS

| | | | |
|---|---|---|---|
| 5,305,786 A * | 4/1994 | Debush | B65D 47/205 137/512.3 |
| 6,651,956 B2 | 11/2003 | Miller | |
| 6,662,977 B2 * | 12/2003 | Gerber | B65D 47/205 222/494 |
| 2003/0062090 A1 * | 4/2003 | Secondo | B05B 11/007 137/853 |
| 2007/0255228 A1 * | 11/2007 | Secondo | B05B 11/007 604/246 |
| 2009/0236374 A1 * | 9/2009 | Pardes | A61F 9/0008 222/494 |

* cited by examiner

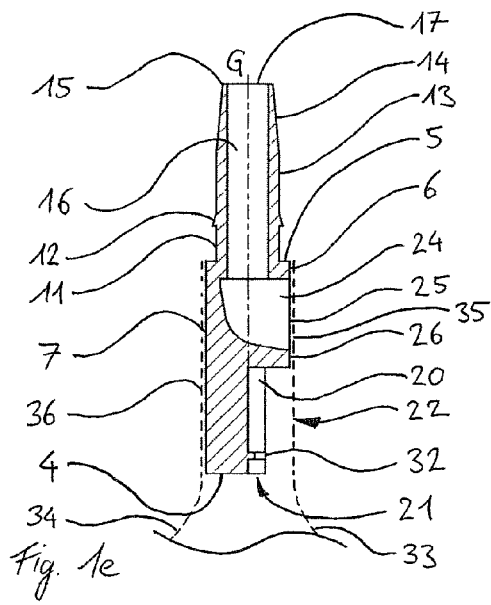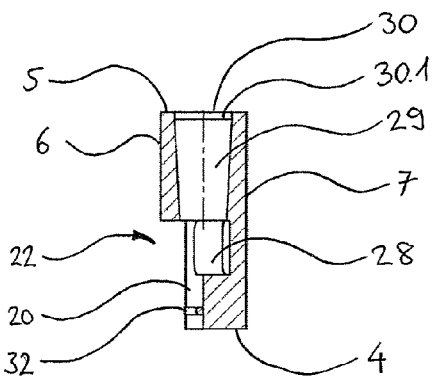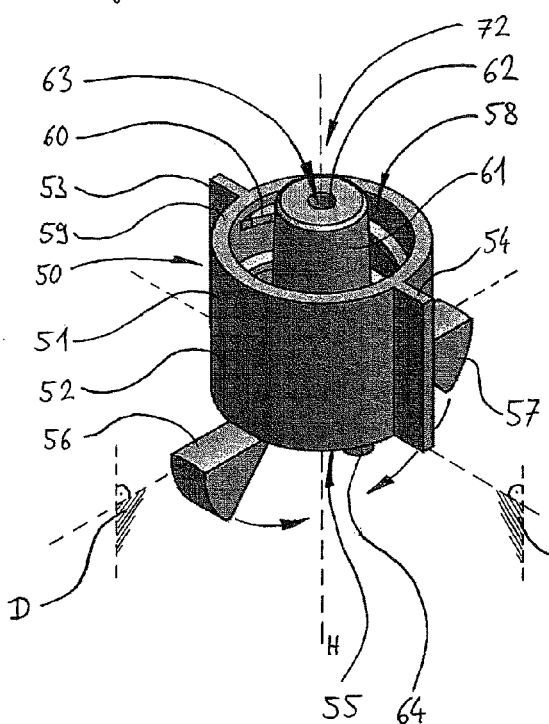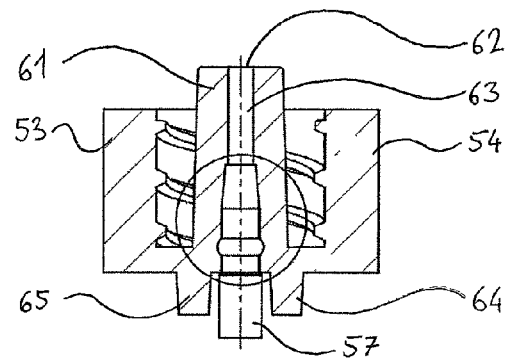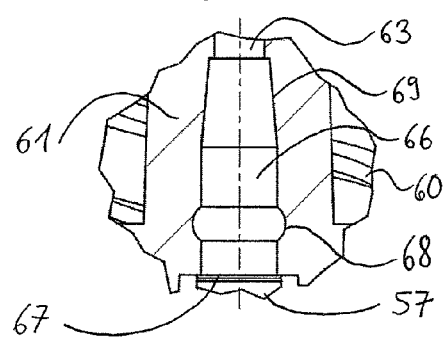

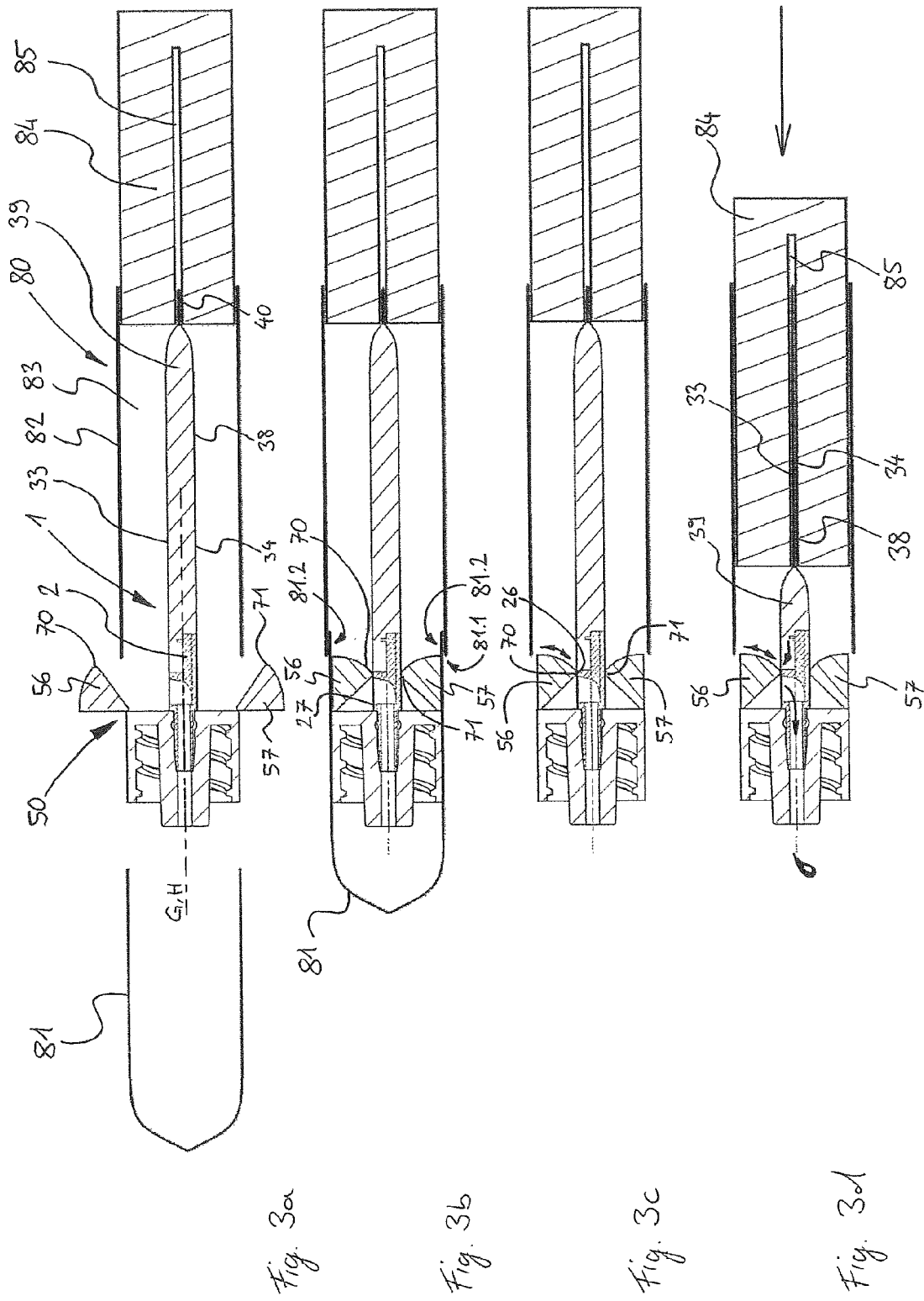

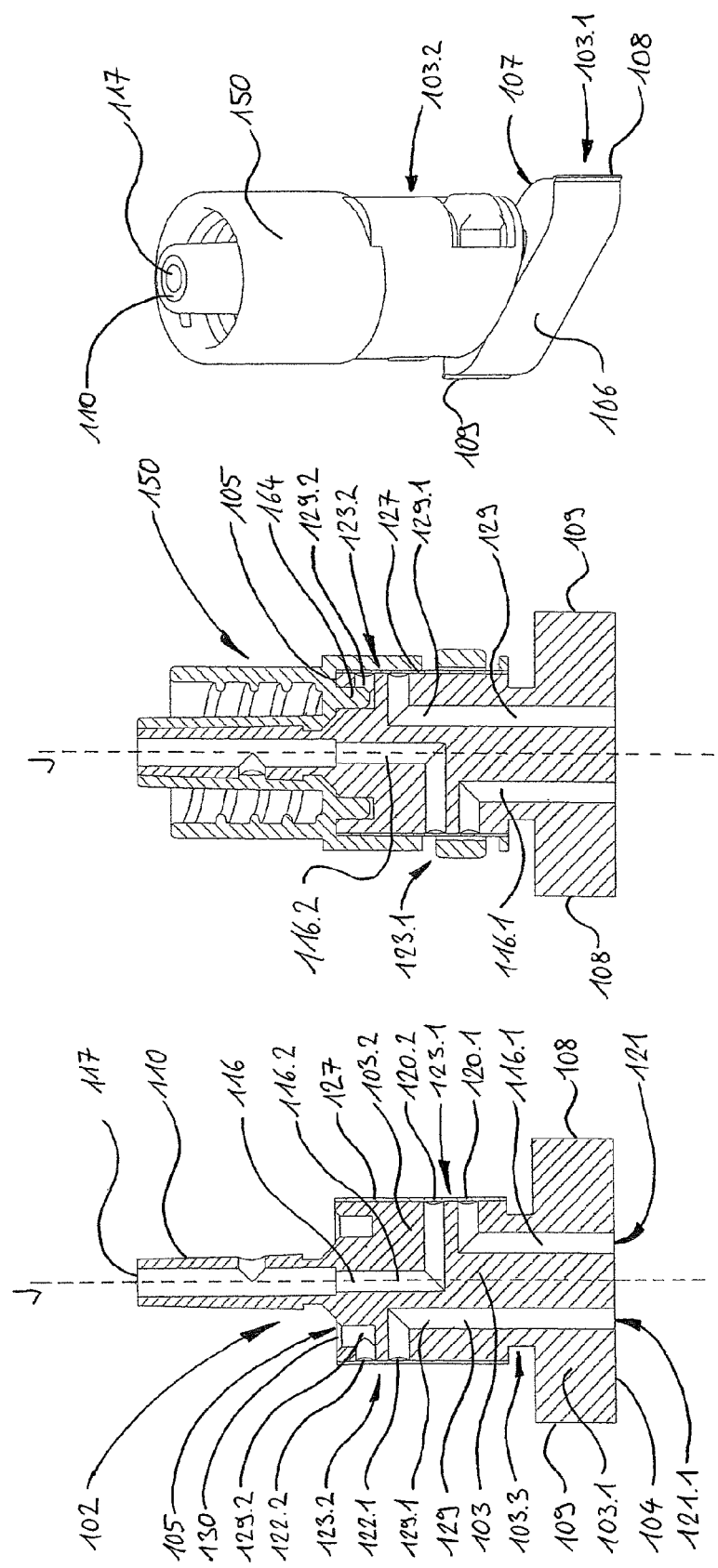

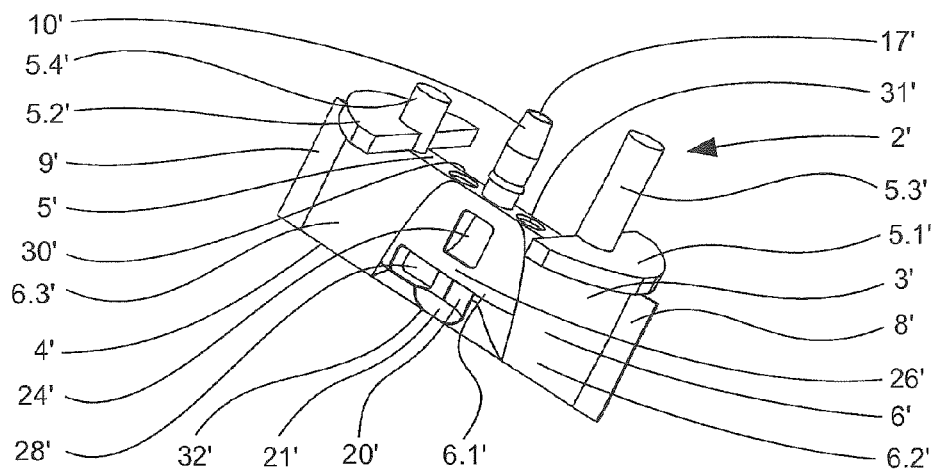
Fig. 7a
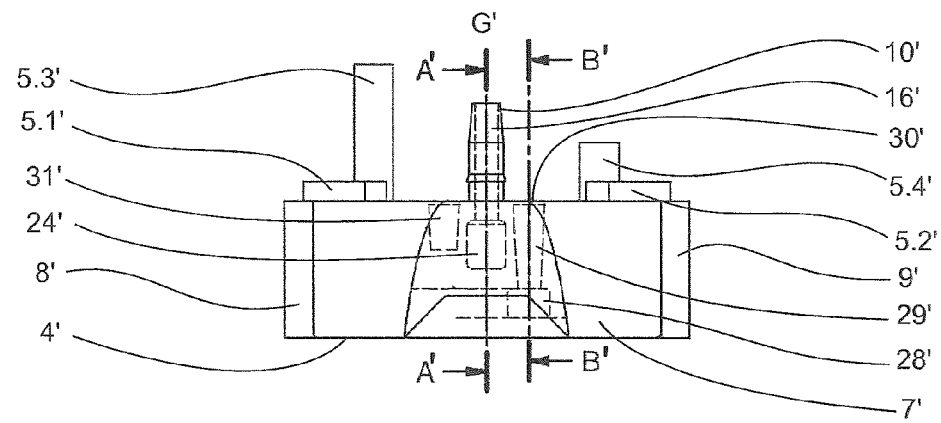
Fig. 7b
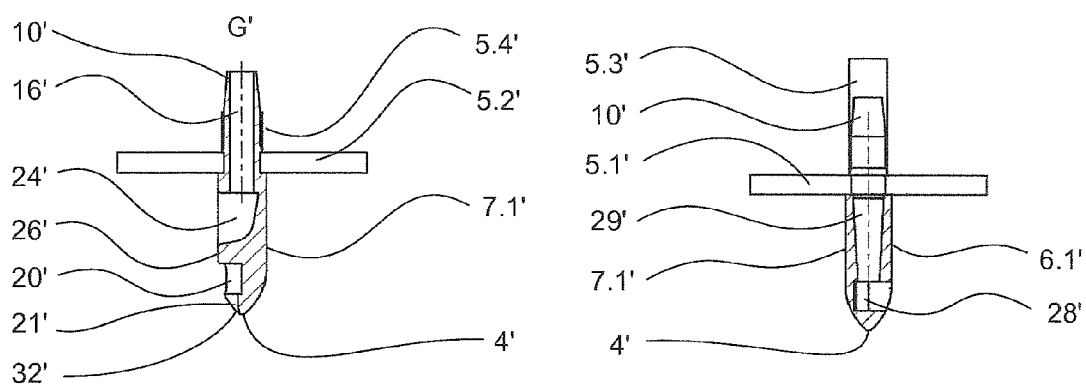
Fig. 7c
Fig. 7d
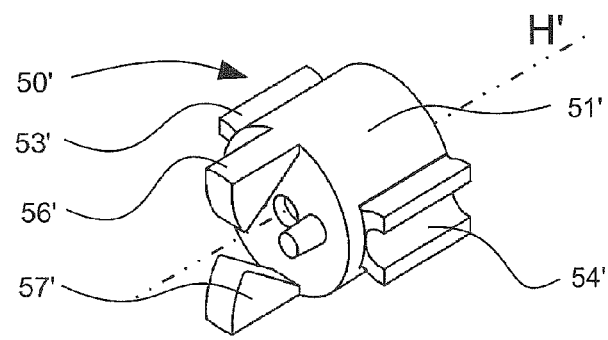
Fig. 8

DEVICE FOR RECEIVING AND DISPENSING A FLUID

TECHNICAL FIELD

A device for receiving or dispensing a fluid, preferably for a fluid comprising a drug, comprising a container, in particular a container which is collapsible at least in regions, and comprising a closure piece, the closure piece comprising a connecting region for the connection of the container. In the connecting region, a removal opening is arranged in such a manner that said removal opening communicates with an interior space in the container. Furthermore, the closure piece comprises a dispensing region in which, in order to dispense the fluid, a dispensing opening is formed, and a dispensing channel which connects the dispensing opening fluidically to the removal opening, wherein a dispensing section of the dispensing channel communicates with the dispensing opening and a removal section of the dispensing channel communicates with the removal opening. The dispensing channel comprises a valve device which, in a closed position, closes the dispensing channel in a fluid-tight manner and, in an open position, permits passage of the fluid through the dispensing channel if there is a positive pressure of sufficient size in a fluid in the removal section.

PRIOR ART

Drugs in general and in particular drugs to be administered parenterally, i.e. bypassing the digestive tract, are decanted after the preparation thereof into a container which can receive one or more portions/doses. As a rule, containers of this type are called a primary pack. For dispensing to a patient, the drug located in the primary pack as a rule has to be transferred into a dispensing device, such as, for example, into a syringe, in the case of a drug which is to be injected.

Examples of a primary pack include glass ampules which have to be opened with a special ampule saw or which are provided with a predetermined breaking point for opening purposes. The drug can be transferred through the opening produced in such a manner into the dispensing device. In the case of the glass ampule, a residue generally has to remain in the ampule, since, otherwise, air can undesirably be sucked up when drawing back the syringe. Subsequent reclosing of the ampule while maintaining the sterility is virtually impossible.

Further primary packs include what are referred to as perforable ampules (vials). The latter have, for example, a self-closing penetration element for the needle of a syringe. For the drawing-back of the syringe, the penetration element is pierced and the drug present in the container is transferred into the syringe (drawing-back of the syringe). The interior space in the perforable ampule remains substantially sterile in this case, and therefore primary packs of this type are suitable for repeated removal of liquid.

However, because of the required transfer into dispensing devices, systems on the basis of primary packs of this type are complicated, and there is an increased risk of contaminating the drug by means of dirt or micro-organisms. In emergency medicine, for example, the opening or piercing of ampules and the subsequent transfer into the dispensing device is, however, tricky under time pressure and possibly in heavily contaminated surroundings.

Other known systems dispense with primary packs and store the drugs directly in the devices provided for the dispensing, such as, for example, syringes. For administering purposes, the dispensing devices can be provided with a hollow needle or cannula which is attached or is glued in place. By application of pressure to a movably mounted piston, the liquid is injected out of the container through the cannula. However, the construction of systems of this type means that they are comparatively expensive. In addition, precautions have to be taken to ensure that the device and the drug remain functional even over a relatively long storage period. For this purpose, piston and injection container are provided with coatings, such as, for example, silicone. Therefore, a substance which has no connection with the actual action of the drug and may have a disadvantageous effect, for example in the case of drugs with a high pH, is stored and administered together with the drug.

U.S. Pat. No. 3,114,369 describes a container which is deformable by finger pressure and which, owing to the positive pressure which can be generated in this manner in the interior space in the container, outputs a liquid through a dispensing opening, for example through a hollow needle. The dispensing opening is sealed by a penetrable membrane which can be pierced by the rear end of the injection needle prior to use. Once, however, the membrane has been pierced, liquid can emerge unhindered, and this may result in, for example, undesirable dripping.

DE 32 24 656 likewise describes a deformable container for storing medicinal liquids, which container can be emptied through a dispensing opening by means of pressing. In this case, a valve device is provided on a closure piece of the container, said valve device preventing a liquid, once the latter has emerged through the valve device, from flowing back into the container. In addition, the valve device ensures that the medicinal liquid contained in the container cannot unintentionally escape. However, because of the construction, the closure piece has pockets and dead spaces, which may result in air pockets, in the valve region. As a rule, direct injection of the fluid from the container into the body of a living organism is therefore not possible. In addition, because of the dead spaces, liquid contaminated with dirt or micro-organisms may remain in the closure piece for an indefinite period, and therefore it is almost impossible to ensure a sterile environment.

It is therefore the object of the invention to overcome the disadvantages of the prior art, and in particular to provide a device for receiving and for dispensing a fluid, in particular for a fluid comprising a drug, which device is simple to construct and produce and simple and safe to handle. Furthermore, it is the object of the invention to provide a device for receiving and dispensing a liquid, which device permits repeated dispensing of fluid without the fluid being able to escape unintentionally or being able to be contaminated by dirt or micro-organisms. Furthermore, it is the object of the invention to provide a device for receiving and dispensing a fluid, which device is suitable for direct parenteral administration of the fluid from the container.

SUMMARY OF THE INVENTION

The object is achieved by the features of claim 1. According to the invention, the device for receiving or dispensing a fluid, preferably for a fluid comprising a drug, comprises a container, in particular a container which is collapsible at least in regions, and a closure piece. The closure piece comprises a connecting region for the connection of the container, wherein a removal opening is arranged in the connecting region in such a manner that said removal opening communicates with an interior space in the container. Furthermore, the closure piece comprises a dispensing region in which, in order to dispense the fluid, a dispensing opening is formed, and a dispensing channel which connects the dispensing opening fluidically to the removal opening. In this case, a dispensing section of the dispensing channel communicates with the dispensing opening and a removal section of the dispensing channel communicates with the removal opening. The dispensing channel comprises a valve device which, in a closed position, closes the dispensing channel in a fluid-tight manner and, in an open position, permits passage of the fluid through the dispensing channel if there is a positive pressure of sufficient size in a fluid in the removal section. The invention is distinguished in that the valve device has two valve openings which are arranged next to each other on a valve surface and are arranged, in particular, on a common valve surface, and of which a first valve opening communicates with the dispensing opening via the dispensing section of the dispensing channel and a second valve opening communicates with the removal opening via the removal section of the dispensing channel, and there is a continuous, flexible membrane which, in the closed position of the valve device, bears against the valve surface so as to be raisable in regions and thus closes off the valve openings from each other in a fluid-tight manner.

It goes without saying that the valve surface can be assembled from a plurality of sections which, for example, butt against one another at an angle or are stepped in relation to one another. However, the two valve openings are preferably arranged on a common valve surface of the closure piece. The flexible membrane can therefore be arranged in a simple manner on the common valve surface and can thus close off the valve openings from each other in a fluid-tight manner.

If a pressure in the fluid in the interior space in the container exceeds a certain threshold value, the flexible membrane can be raised from the valve surface in the region between the valve openings by the fluid in the removal section, as a result of which a passage for the fluid is created between valve surface and membrane. The fluid can therefore pass to the adjacently arranged valve opening on the dispensing side and therefore into the dispensing section of the dispensing channel. In other words, the flexible membrane is arranged so as to be raisable on the valve surface in such a manner that, depending on a positive pressure in a fluid in the removal section of the dispensing channel, the membrane can be raised and the valve device can therefore be brought into an open position. In the open position of the valve device, the flexible membrane therefore permits a fluid connection between the two sections of the dispensing channel. Membrane and valve surface here delimit a fluid channel producing the fluid connection. Owing to the positive pressure required, it is ensured that, even in the open position of the valve device, possible fluid residues do not flow back out of the section on the dispensing side into the section on the removal side.

The flexible membrane bears against the valve surface in a fluid-tight manner and so as to be raisable, in particular in a region between the valve openings. In further regions of the valve surface, the membrane can advantageously be fixedly connected to the valve surface, i.e., for example, can be fastened so as not to be raisable. In the open position of the valve device, a fluid channel fluidically connecting the valve openings can therefore be defined between the valve openings. The flexible membrane here can advantageously also be of elastic design, and therefore, when the positive pressure decreases, the membrane can automatically be lowered again onto the valve surface and/or, in the lowered state, can exert pressure on the valve surface in order to provide better sealing of the fluid.

For simple generation of the positive pressure in the fluid, the container is advantageously designed so as to be collapsible at least in regions (see below). In other embodiments, the container can be manufactured, for example, as a bellows made from an elastic material or else, if required, can have fixed walls, i.e. can be of non-collapsible design. In this case, a positive pressure can be generated in a fluid in the container, for example, with a piston in the manner of a syringe. It goes without saying that these embodiments of collapsible containers are merely exemplary and, for further possible embodiments, reference is made to the extensive and relevant prior art.

According to the invention, the valve device of the closure piece is designed in such a manner that, in an inoperative state of the valve device, i.e. when the membrane bears in the raisable region against the valve surface, the removal section and the dispensing section are separated off from each other by the flexible membrane. For this purpose, the flexible membrane preferably bears in a fluid-tight manner against the valve surface, at least in the border regions of the valve openings.

Owing to the construction, the valve device has bidirectional functionality. In the event of a positive pressure of sufficient size in a fluid in the dispensing section of the dispensing channel, fluid can also pass in the reverse direction analogously to the above-described passage from the removal section to the dispensing section. This has the advantage that the container can basically be filled by the dispensing channel via the dispensing opening. For example, partially evacuated bags or tubes which are provided with the closure piece and can be filled in this manner are conceivable. The device and the container or the closure piece can also comprise a ventilation device, for example a one-way valve, and therefore any air from the filling operation can escape out of the interior space in the container.

A threshold value of the positive pressure required for producing the fluid connection between the valve openings is advantageously selected in such a manner that an inadvertent passage of the fluid between the two sections is substantially prevented. Should an unintentional passage nevertheless occur, by the container, for example, being inadvertently squeezed, the fluid passes from the container to the outside, and the container contents are not contaminated. Different threshold values can be set by selection of the membrane flexibility, and therefore the valve device can be adapted to the requirements of the particular application (for example to a fluid viscosity).

The fluid which can be present in the container preferably comprises a drug, in particular a drug to be used parenterally, orally or topically. However, the advantages of the construction according to the invention are also directly accessible in other medicinal spheres. An exemplary and non-exhaustive list includes the container also being suitable, for example, for use with disinfectants and cleaning agents or in rinsing. However, conceivable applications of the device for receiving and dispensing a fluid are not limited to the medicinal sphere. The device according to the invention is also particularly suitable, for example, for cosmetic fluids or in the foodstuff sphere, for example for viscous foodstuffs, such as sauces (ketchup, mustard, etc.). As a rule, full maintaining of the sterility of the fluid in the container is not required in said spheres. However, in view of the application of fluids of this type on the human body or because of the taking of said fluids, attention should also be paid in this case to particular hygiene, and therefore the device according to the invention may be advantageous also in these applications. In general, the device according to the invention is suitable for all application spheres in which there are more exacting requirements in order to avoid contamination of a fluid in the device with dirt or micro-organisms, and fluid dispensing which can be controlled and metered in a simple manner is desirable.

The container of the device according to the invention is particularly preferably designed so as to be, at least partially, collapsible, preferably in the form of a bag or tube. As a rule, a container wall of the container here is designed so as to be flexible at least in regions, and therefore a positive pressure can be built up in the container by compression of the container wall. In other words, at least one region of the container is designed and produced in such a manner that, at least in this region, a positive pressure can be built up in the interior space in the container by means of deformation of the container wall such that a fluid present in the interior space in the container can be pressed through the removal opening into the dispensing channel of the closure piece and can be fed to the dispensing opening via the valve device.

In this manner, for example, by squeezing with the fingers or via a dispensing device, the required positive pressure can be generated in the fluid in order to bring the valve device from the closed position into the open position. In particular, the container can have container walls which are manufactured, for example, from a film material, lie one above another, for example, in two layers and are connected to one another in the border regions via a connecting seam (bag-like container). The two film layers here can be provided by separate film layers or by an individual folded film layer. The connecting seam can comprise, for example, an adhesive bond or a weld. However, the container may also have a film which is rolled to form a tube and is connected to itself and is pressed flat at one longitudinal end of the tube and, for example, is welded (tube-like container).

The container wall preferably comprises a plastic, in particular a coated plastic, preferably a laminate. An inner layer, i.e. a layer which bounds the interior space, can be designed, for example, so as to be particularly compatible to a specific fluid, whereas an outer layer determines, for example, the mechanical properties of the container.

In the connecting region, the closure piece can have a coupling means, such as, for example, a screwthread or a bayonet for the connection of the container, for example in the manner of a toothpaste tube, onto which the closure piece with the valve device is screwed in place of a lid.

However, in a particularly preferred embodiment, in the connecting region, the closure piece has at least one connecting surface to which a connecting section of the container wall is directly fastenable. Closure piece and container wall therefore form a fixedly connected unit if the container wall is fastened to the connecting surface. The container wall is preferably welded or adhesively bonded to the connecting surface, in particular, for example, is welded by ultrasound or laser. This gives rise, for simple production, to a secure connection which ensures a fluid-tight and non-releasable connection of the container to the closure piece.

The connecting section of the container wall is advantageously designed so as to be flexible, and the valve surface with valve openings is arranged on the at least one connecting surface of the closure piece in such a manner that a region of the connecting section of the container wall forms the flexible membrane of the valve device, in particular covers the valve openings. The container wall can thereby carry out an additional function as part of the valve device, which permits a cost-effective and simple construction of the device according to the invention. In variants, the flexible membrane can also be designed as a separate part independently of a container wall. For example, a flexible sleeve, which is pulled over the valve surface formed, for example, on a lateral area of a cylindrical section, is conceivable.

In order further to simplify the construction of the device, in a preferred embodiment, in the connecting region, the closure piece has a section of substantially cylindrical design, wherein the at least one connecting surface is arranged on an outer lateral area of the cylindrical section.

By means of the cylindrical section, the closure piece can be inserted in a simple manner into an opening on the end side of a container, for example designed in the shape of a tube, and can be fastened there. In variants, the section can also be of conical design corresponding to a, for example, diverging shape of the container. However, the closure piece preferably has a section which is of cylindrical design and which can be used for a multiplicity of shapes of the container wall, such as, for example, tubes and bags. Depending on requirements and/or shape of the container, the cylindrical section can have, for example, a circular base surface, but may also have a polygonal or elliptical cross section.

In a preferred embodiment, in addition to the at least one connecting surface, the lateral area of the cylindrical section comprises a further connecting surface, wherein the two connecting surfaces converge pairwise at a common edge, in particular arranged parallel to the cylinder axis, and therefore the cylindrical section has a substantially lenticular base surface.

For this purpose, the two end surfaces are preferably of curved design and converge at the respectively common edge in such a manner that the container walls, which are fastened to the connecting surfaces, come to lie on one another without a gap at the edges. Lenticular is understood here in analogy to the cross section of a biconvex optical lens. The connecting surfaces here form the lateral area of the closure piece and converge in a direction transversely with respect to the cylinder axis at a respectively common edge. The connecting surfaces here are curved, preferably without edges, as a result of which the container walls can be fastened thereto smoothly and without bends. It goes without saying that the lens shape of the cross section can be flattened or modified in another manner.

The closure piece can therefore be connected in a simple manner to a container designed in the form of a bag or tube, with the connecting piece being inserted into a connecting seam of the container wall or of the container walls. The connecting sections of the container walls engage around the closure piece at the connecting surfaces and can be arranged directly on one another at the edges of the lateral area. The removal opening is advantageously formed on the base surface of the closure piece, which base surface is arranged in the interior space in the container and bounds said interior space. The dispensing region is preferably arranged opposite the base surface in the direction of the cylinder axis and advantageously comprises an end side arranged substantially parallel to the base surface.

The device according to the invention can basically be filled, as described above, via the dispensing channel. However, the closure piece advantageously has an additional filling channel for filling the container, said filling channel fluidically connecting a connecting opening for the connection of a fluid source in the dispensing region and a filling opening in the connecting region, wherein the filling opening communicates with the interior space in the container.

The additional filling channel with associated connecting opening and filling opening simplifies the filling of the container via the closure piece. The fluid can be introduced into the container via the filling channel, wherein the dispensing channel can function as a ventilation channel for the escape of air possibly present in the interior space in the container. The container can therefore be completely filled with the fluid without air pockets and is therefore suitable in particular also for medicinal fluids to be administered parenterally.

As a rule, the container is filled under controlled conditions, i.e. optionally under sterile conditions. Therefore, the filling channel which is provided for one-time use during the filling operation does not have to include special precautions for the protection of the interior space in the container against undesirable contamination. The filling channel can therefore be designed in particular in a simple manner without a valve device. However, it goes without saying that a valve device analogously to the valve device of the dispensing channel can also be formed in the filling channel, should this be desired.

By the connecting opening being arranged in the dispensing region, a fluid source can be connected from the outside in a simple manner. In particular, the connecting opening can be formed on an end side of the closure piece in the vicinity of the dispensing opening, and therefore synergies in respect of, for example, connecting caps or coupling means in the connecting region can be used for the two openings (see below).

An embodiment of the device is particularly advantageous, in which the closure piece comprises a coupling element in the dispensing region, said coupling element being designed for directly or indirectly coupling the device to an additional component or to a fluid-conducting system. The coupling element here preferably comprises a fluid channel which is connected to the dispensing opening and leads to a dispensing opening of the coupling part.

The coupling element is preferably formed on an end side of the closure piece, and therefore the device can be connected in a simple manner. The coupling element can have, for example, a screw connection or plug-in connection or a bayonet. However, the coupling element preferably comprises a coupling cone which tapers away from the closure piece and permits a fluid-tight and secure coupling in a known manner by means of a conical interlocking connection. The fluid channel advantageously runs in the longitudinal direction of the coupling cone. The coupling cone can be designed in particular as a known Luer lock connection, preferably as an outer cone of a Luer lock. The coupling means of the closure piece is advantageously integrally formed directly on the closure piece, in particular is formed as a single piece with the closure piece.

It goes without saying that there does not need to be a coupling element and, for certain applications, a hollow needle or rinsing needle, for example, can advantageously be fastened directly to the closure piece, for example can be inserted into the dispensing opening.

In particular in the sphere of dialysis systems, a further embodiment of a coupling element is preferred, which coupling element comprises a tubular housing, such as, for example, a tube section, with a lumen for conducting a fluid, such as, for example, the body fluid of a dialysis patient. The housing has at least one access opening which is formed in the housing wall and communicates with the dispensing opening of the closure piece of the device. The fluid can be introduced from the device into the lumen through the access opening. Furthermore, a valve device is advantageously present in the coupling element, said valve device permitting passage of liquid through the access opening into the lumen and blocking said passage in the opposite direction.

In this case, the coupling element advantageously has at least one additional injection port via which a medication can be introduced into the lumen with an external device. "Injection port" refers here and below to a closable or self-closing access opening for the fluid-tight coupling of a medicinal medication-dispensing device to a fluid conducted in the lumen. Similarly, depending on the design of the injection port, samples of the fluid conducted in the lumen can also be removed if the need arises.

Injection ports of this type can be provided with a medicinal-device connection which is hygienically acceptable and simple to clean, such as, for example, what is referred to as a "swabable valve" according to U.S. Pat. No. 6,651,956 (Halkey-Roberts Corporation). However, injection ports within the present understanding may also comprise a penetrable and self-sealing septum, and therefore medication can also be introduced with an injection needle. The septum here preferably covers an opening in the housing wall and is welded to the housing, for example, by means of an ultrasonic method. The cross section of the lumen is therefore only slightly changed, if at all, by the septum, and therefore the fluid can flow substantially unaffected in the lumen.

The closure piece of the device is advantageously connected, preferably with the end side in the dispensing region, laterally on the outside of the tubular housing, and therefore the two ends of the tubular housing are free for the connection to a fluid-conducting system. Closure piece and housing here can be designed as a single-piece molded part. On the end sides, the tubular housing can have coupling devices for the connection at one or both ends to the fluid-conducting system. In variants, the tubular housing can be closed off on one side or can be designed directly as a section of a hose or tube.

In a preferred embodiment, the device comprises an additional connecting cap which is attachable in the connecting region to the closure piece. The connecting cap is preferably designed in such a manner that it is attachable to a coupling element of the closure piece, which, if need be, is present, and is couplable thereto.

In the attached state, the connecting cap advantageously closes the connecting opening in the dispensing region of the closure piece. For this purpose, the connecting cap can have at least one closure pin which is arranged and is dimensioned in such a manner that, when the connecting cap is attached, said closure pin can be introduced into the connecting opening on the closure piece and closes said connecting opening in a fluid-tight manner. In this case, the connecting cap can be attached after the container is filled, and therefore the connecting opening is sealed such that fluid cannot emerge or possible soiling cannot enter the filling channel. For a plurality of possible orientations for the attachment of the connecting cap to the closure piece, a plurality of closure pins can be designed in such a manner that, in each possible orientation of the connecting cap, one of the closure pins is arranged in the connecting opening.

The connecting cap and the closure piece advantageously comprise latching means which can be brought into engagement with one another for latching of the connecting cap in the attached state on the closure piece and which prevent the connecting cap from being able to be removed unintentionally from the closure piece.

The connecting cap preferably comprises a coupling means for the fluid-communicating coupling of the dispensing opening to a fluid-conducting system, in particular to an outer cone of a Luer lock. The coupling means here preferably has a fluid channel such that, in the attached state of the connecting cap, the fluid channel communicates with the dispensing opening of the closure piece.

However, the connecting cap can also be directly provided with a hollow needle, rinsing needle or other device for dispensing or administering the fluid, which, when the connecting cap is attached, communicates with the dispensing opening of the container and permits, for example, direct parenteral administration of the fluid by means of injection or infusion.

The coupling means of the connecting cap can be designed according to a standardized standard. In this case, the container can be coupled to a standardized connection of a fluid-conducting system via the connecting cap independently of a design, which at any rate is non-standardized, of the coupling element of the closure piece. The connecting cap in this case functions as a connecting adapter.

It goes without saying that the coupling means of the connecting cap can be adapted to specific requirements. An embodiment of a coupling means of the connecting cap that is preferred in particular in the sphere of dialysis systems is therefore formed analogously to the above-described coupling means of the closure piece with a tubular housing. However, in this case, the connecting cap (and not the closure piece itself) is connected laterally to the tubular housing and, for example, is integrally formed thereon. The connecting cap together with the tubular housing can be designed as a single-piece molded body. The connecting cap here is configured in such a manner that, when the connecting cap is attached to the closure piece, the dispensing opening of the closure piece communicates with the access opening in the tubular housing.

It goes without saying that the connecting cap can also be designed without coupling means and has, for example, application means for the fluid. In particular, for example, a sponge can be provided on the connecting cap, said sponge being able to be directly supplied with the fluid from the container via a connecting-cap fluid channel which communicates with the dispensing opening of the closure piece. An embodiment of this type is particularly advantageous, for example, for a disinfecting fluid, since the fluid can be dispensed directly from the device according to the invention to the sponge for application. In this case, the application means can have, for example, a plurality of layers of protective coverings consisting of, for example, mesh and/or microfilters, which are pulled over the sponge. In particular, the individual layers can be designed so as to be removable, and therefore, following rough cleaning, a first layer can be removed in order to carry out fine cleaning with a second layer which is still clean. For the final disinfection, the second layer can also be removed, and therefore the final disinfection can be carried out with the sponge which is still clean. It goes without saying that, depending on requirements, further or fewer layers of suitable materials may also be present. Similarly, it goes without saying that a sponge which is encased by multiple layers and is intended for the application of a disinfectant in a plurality of steps can advantageously also be used detached from the device according to the invention for receiving and dispensing a fluid in the case of other devices for dispensing a fluid.

In other embodiments, the connecting cap can also be designed solely for the fluid-tight closure of the connecting opening and/or of the dispensing opening of the closure piece.

The connecting cap preferably has a receiving space which is of substantially complementary design to the coupling element of the closure piece and in which the coupling element is receivable when the connecting cap is attached.

The receiving space is preferably formed in the connecting-cap coupling means, which is advantageously designed as a Luer outer cone. A coupling element of the closure piece of the container, which coupling element is designed, for example, as a coupling cone, can therefore be accommodated in a space-saving manner, similarly to stacked beakers, in the connecting cap or in the coupling means thereof.

The connecting cap preferably has a closure means which is designed in such a manner that, when the connecting cap is attached, the valve device is fixable in the closed position by the closure means.

The closure means therefore permits blocking of the valve device in the closed position, and therefore the container is securely closed, for example for storage purposes, and therefore no fluid can emerge even in the event of a corresponding positive pressure in the interior space in the container. In other words, the valve device is fixed in the closed position in such a manner that the dispensing channel is interrupted, and therefore the fluid or dirt can neither enter into nor emerge from the container through the dispensing channel.

The closure means is advantageously designed and arranged in such a manner that the flexible membrane is fixedly pressable onto the valve surface by the closure means in the region between the valve openings.

The closure means here can be formed movably, in particular in a spring-mounted manner, on the connecting cap. The closure means is preferably in a standby position before the connecting cap is attached to the closure piece. After the connecting cap is attached, the closure means can be brought, for example, by a user or a production machine, into an active position, in which said closure means interacts with the flexible membrane. In the active position, the closure means can preferably be blocked in a closed position in such a manner that the membrane is pressed by the closure means onto the valve surface in a fluid-tight manner. The closure means can be blocked, for example, via a closure cap of a dispensing device into which the device according to the invention is insertable or is inserted. In the attached state, the closure cap in this case interacts with the closure means, for example blocks the closure means, in such a manner that the latter securely clamps the membrane between valve surface and closure means. In this case, in order to use the dispensing device, the closure cap is removed and therefore, although the closure means remains in the active position, said closure means takes up a release position. Although, in the release position, the closure means can continue to interact with the membrane, the membrane is, however, raisable from the valve surface, and therefore, when the dispensing device is actuated, the fluid can be dispensed from the device. The closure means can continue, for example, to press the membrane against the valve surface, but permits raising of the membrane from the valve surface. For this purpose, the closure means can be mounted, for example, in a spring-mounted manner on the connecting cap. Depending on the design of the closure means or the mounting on the connecting cap, a threshold value for the required positive pressure for the transfer into the open position of the valve device can therefore be predetermined by the support pressure in the release position substantially independently of the material properties of the flexible membrane.

In principle, however, the closure means can also be attached fixedly and immovably to the connecting cap and can directly or indirectly block the flexible membrane against raising from the valve surface simply by the connecting cap being attached and without further manipulating. In this case, for release purposes, the closure means can be broken off, for example, at a predetermined breaking point, for example by a user. In this case, the membrane is preferably also of elastic design, and therefore said membrane also bears against the valve surface without closure means. In principle, embodiments entirely without closure means are also conceivable, but, in this case, when the device is mounted, there is the risk, inter alia, of an unintentional dispensing of fluid.

Depending on requirements, the device can advantageously comprise a supporting structure to which the container is fixedly connected. This is advantageous in particular in the case of an at least partially collapsible container. Containers of this type can be deformed in an unforeseeable manner during filling, for example in the case of flexible container walls. By a preferably substantially rigid supporting structure being present, a fixed shape of the container can be predetermined in the region of the supporting structure. The supporting structure here can be designed as a frame or can be provided by a housing in which the container is arranged. The container is preferably fixedly connected to the supporting structure in border regions of the container walls. In particular in the case of a container in the shape of a bag, the connecting regions of the container walls can be fixedly connected to the supporting structure, for example welded or adhesively bonded, at the edge. In this case, the container walls can be clamped in the supporting structure.

The supporting structure is preferably provided by a dispensing device with a receiving space which is bounded by a housing. In this case, the container is arranged in the receiving space and, in addition, is fixedly connected to the housing. Exemplary embodiments of corresponding dispensing devices are described further below. In this case, the dispensing device forms an integral part of the device according to the invention. The container, in particular in the case of a bag-shaped design, is preferably clamped with longitudinal borders of the container walls between two housing parts of the dispensing device or is fastened to the inner side of the receiving space.

The concept according to the invention is also extended to a closure piece for a device for receiving and dispensing a fluid, in particular for a device according to the invention, as described in the present case. The closure piece according to the invention is defined by the features of claim 13. According to this aspect of the invention, a closure piece for a container comprises a connecting region for the connection of a container, in particular a container wall, wherein a removal opening is arranged in the connecting region in such a manner that said removal opening communicates with an interior space in the container when the container is connected to the closure piece. Furthermore, the closure piece comprises a dispensing region in which, in order to dispense the fluid, a dispensing opening is formed, and also a dispensing channel which connects the dispensing opening fluidically to the removal opening, wherein a dispensing section of the dispensing channel communicates with the dispensing opening and a removal section of the dispensing channel communicates with the removal opening. The dispensing channel here comprises a valve device which, in a closed position, closes the dispensing channel in a fluid-tight manner and permits passage of the fluid through the dispensing channel if there is a positive pressure of sufficient size in a fluid in the dispensing channel. This aspect of the invention is distinguished in that the valve device has two valve openings which are arranged next to each other on a valve surface, in particular are arranged on a common valve surface, and of which a first valve opening communicates with the dispensing opening via the dispensing section of the dispensing channel and a second valve opening communicates with the removal opening via the removal section of the dispensing channel, and there is a continuous, flexible membrane which, in the closed position of the valve device, bears in a raisable manner against the valve surface and thus closes off the valve openings from each other in a fluid-tight manner.

The concept according to the invention also relates, in detachment from the device according to the invention or the closure piece, to a valve device by itself, said valve device being suitable for a closure piece, as described above. The valve device here comprises two valve openings which respectively communicate with a section of a fluid channel and are arranged next to each other on a valve surface, in particular on a common valve surface, wherein there is a continuous, flexible membrane which, in a closed position of the valve device, bears against the valve surface in a raisable manner and closes off the valve openings from each other in a fluid-tight manner.

Modifications and preferred embodiments of the closure piece and of the valve device by itself emerge directly from the above description in conjunction with the device according to the invention for receiving and for dispensing a fluid.

Furthermore, the invention also relates to a dispensing device for a device for receiving and dispensing a fluid, in particular for a device according to the invention described in the present case, wherein the fluid is preferably a liquid, in particular comprising a drug. The dispensing device has a receiving space in which the device for receiving and dispensing a fluid can be arranged, and comprises an actuating device with which a positive pressure for dispensing the fluid can be generated in the interior space in a container of the device for receiving and dispensing a fluid. The container is preferably of at least partially deformable design, and therefore the positive pressure can be generated in a simple manner by deformation of a region, provided therefor, of the container arranged in the receiving space. It goes without saying that the dispensing device can be produced and sold both by itself and with a device for receiving and dispensing a fluid already arranged therein.

The actuating device is preferably designed in such a manner that, upon actuation, the container is compressed, or is preferably squeezed. Squeezing here can be achieved, for example, by an actuating-device plunger which is slit longitudinally in the actuating direction and can be pushed in the longitudinal direction into the receiving space. The plunger is pushed by two halves bounding the slot from a longitudinal end of the bag that is opposite the closure piece such that the slot is over the bag. The container walls of the bag are compressed in the slot by the advancing of the plunger, and therefore the positive pressure required for dispensing a fluid is generated in the interior space. The plunger here can be actuated directly by a user, or else can also be displaced in the receiving space by motor, for example via a spindle or rack, or indirectly by a user.

In a further preferred embodiment, the actuating device of the dispensing device has a plunger which can be introduced, for example pivoted or pushed, into the receiving space from the side, i.e. substantially transversely with respect to the longitudinal direction. In this case, the required positive pressure in the container is achieved by squeezing together the container between plunger and a region of the inner wall of the receiving space.

In both cases, the plunger is designed and is matched to the receiving space in such a manner that the fluid can be discharged from the container as completely as possible. It goes without saying that the actuating devices described above by way of example for a bag are also suitable for a tube or other collapsible containers.

The invention also relates to a method for filling a device, as described in the present case. If the device comprises a filling channel, the method comprises, in a first step, blocking the valve device of the dispensing channel. For this purpose, for example, the flexible membrane can be pressed from the outside onto the valve surface between the valve openings in order to block the valve device. This can take place mechanically via a corresponding device of the filling device. It is therefore ensured that, during the filling, fluid from the container cannot emerge through the dispensing channel and through the outlet opening. If the device only comprises one dispensing channel and is filled via the latter, the step of blocking the valve device is dispensed with.

In a further step, the filling device is coupled to the dispensing channel of the closure piece of the device, or, in the case of a device with a filling channel, is coupled to the filling channel of the closure piece. For this purpose, the filling device can have, for example, a filling needle which can be introduced into the corresponding fluid channel, preferably in a self-sealing manner.

In a further step, the fluid is fed to the container by the filling device. Depending on the connection of the filling device, this takes place via the dispensing channel or the filling channel. Subsequently, the removal opening in the connecting region is closed off from the interior space in the container. The closure can take place, for example, by squeezing off the flexible membrane at the removal opening, for example at a squeezing-off rib of the closure piece. The squeezing-off can take place mechanically via a corresponding device of the filling device. If the filling device is connected to the filling channel, the filling opening is also closed off from the interior space in the container. The interior space in the container is thereby completely closed off to the outside.

In a further step, the filling device is decoupled. By closing off the removal opening and optionally the filling opening in the previous method step, the fluid is prevented from being able to emerge out of the container. If, in the event of a filling channel being present, the valve device is blocked, the blocking is stopped after the filling device is decoupled.

The closure piece is subsequently closed with a closure cap and/or other closure means. In particular, firstly a connecting cap, which is closed in turn by a closure cap, can be attached to the closure piece. The dispensing opening and optionally the connecting opening of the filling channel are closed in the process (as described above). After the closure, the removal opening and optionally the filling opening can be opened up. The device is therefore filled and closed and is ready for use.

Further advantageous embodiments and combinations of features of the invention emerge from the description of details below and the entirety of the patent claims.

DESCRIPTION OF THE DRAWINGS

Schematically in the drawings used for explaining the exemplary embodiments:

FIG. 1b shows a lateral exterior view of the closure piece according to FIG. 1a;

FIG. 1c shows an exterior view of a base surface of the closure piece according to FIG. 1a;

FIG. 1d shows an exterior view of an end side of the closure piece according to FIG. 1a;

FIG. 1e shows a sectional view of the closure piece according to FIG. 1a in the plane A;

FIG. 1f shows a sectional view of the closure piece according to FIG. 1a in the plane B;

FIG. 2a shows an outer oblique view of a connecting cap for the closure piece according to FIG. 1a;

FIG. 2b shows a sectional view of the connecting cap according to FIG. 2a in the plane C;

FIG. 2c shows a detail of the sectional view of the connecting cap according to FIG. 2b;

FIG. 3a shows a sectional view in the longitudinal direction through a dispensing device with a device according to the invention arranged therein;

FIG. 3b shows a view of the dispensing device according to FIG. 3a with an attached closure cap;

FIG. 3c shows a view of the dispensing device according to FIG. 3a without a closure cap with closure means in the release position;

FIG. 3d shows a view of the dispensing device according to FIG. 3a, after actuation and partial dispensing of a fluid from the device according to the invention;

FIG. 4a shows a sectional view in the longitudinal direction through a further embodiment of a closure piece for a device according to the invention for receiving and dispensing a fluid;

FIG. 4b shows a sectional view in the longitudinal direction through the closure piece according to FIG. 4a with an attached closure cap;

FIG. 4c shows an outer oblique view of the closure piece according to FIG. 4a with an attached closure cap;

FIG. 7a shows an outer oblique view of a further embodiment of a closure piece for a device according to the invention;

FIG. 7b shows a lateral exterior view of the closure piece according to FIG. 7a;

FIG. 7c shows a sectional view of the closure piece according to FIG. 7a in a center plane;

FIG. 7d shows a sectional view of the closure piece according to FIG. 7a in a parallel plane offset with respect to the sectional plane of FIG. 7c;

FIG. 8 shows an outer oblique view of a further embodiment of a closure cap;

FIG. 9b shows an outer oblique view of an inner side of a housing part of the dispensing device of FIG. 9a;

In principle, identical parts are provided with the same reference numbers in the figures.

WAYS OF IMPLEMENTING THE INVENTION

Figure 1B:
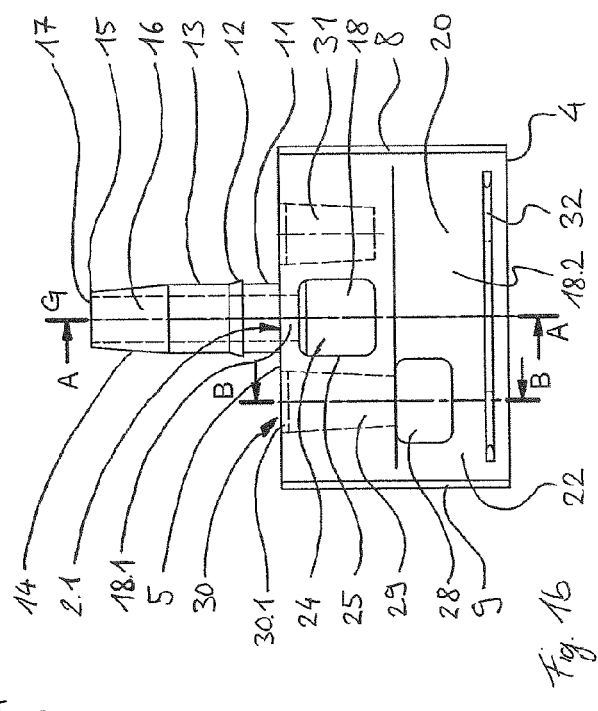
Figure 1D:
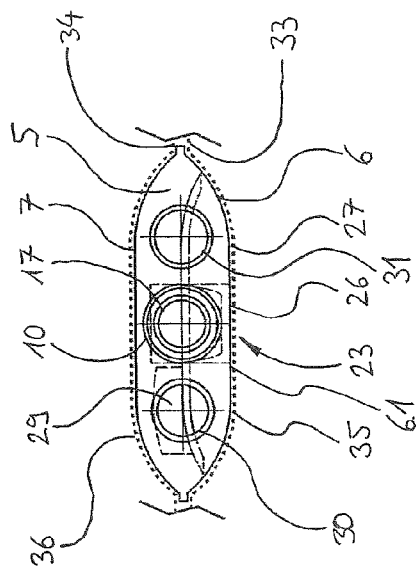
Figure 1A:
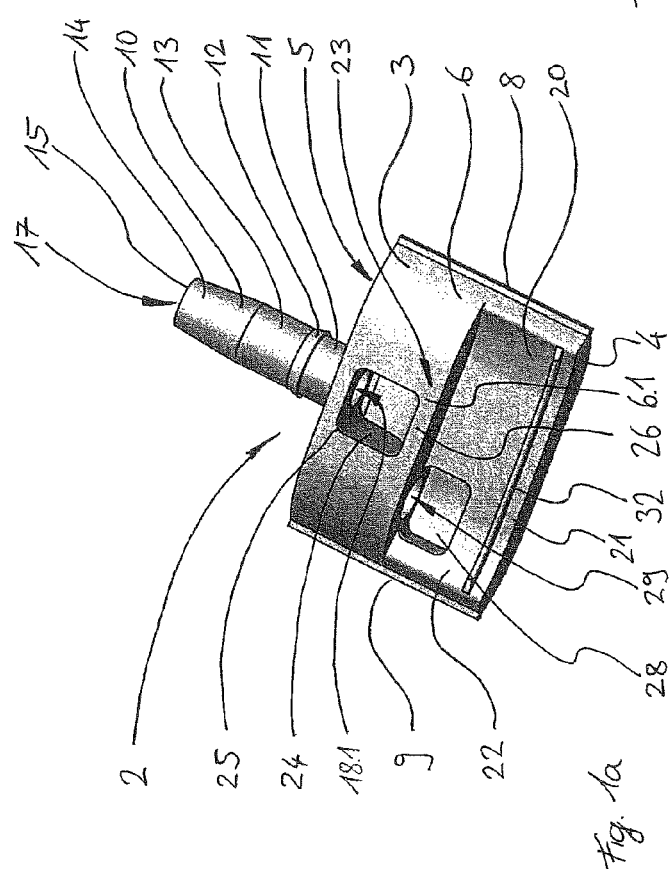
FIG. 1a shows an outer oblique view of a closure piece for a device according to the invention.

FIG. 1a shows an outer oblique view of a closure piece 2 for a device 1 according to the invention (see FIGS. 3a-3d). The closure piece 2 comprises a cylindrical main body 3 with a lenticular base surface 4 and a likewise lenticular end surface 5 oriented parallel to the base surface 4. A direction toward a base-side longitudinal end of the cylindrical main body 3 or beyond the base-side longitudinal end is referred to below by "downward" or "at the bottom". Correspondingly, a direction toward an end-side end or beyond the latter is referred to by "upward" or "at the top".

A lateral area of the cylindrical main body 3 comprises two connecting surfaces 6 and 7 which converge pairwise at respective edges 8 and 9 oriented in the direction of a cylinder axis G. The edges 8 and 9 here are arranged opposite each other with respect to the cylinder axis G. In the present case, the edges 8 and 9 are designed as longitudinal webs which bound the connecting surfaces 6 and 7.

A coupling element 10 is formed on the end side 5 of the main body 3, said coupling element extending away from the end side 5 along the cylinder axis G. In a section 11 in the vicinity of the main body, the coupling element 10 is of circular-cylindrical design. The circular-cylindrical section 11 is adjoined by a latching means 12 which is designed as an annular bead and projects outward radially with respect to the cylinder axis G. The bead 12 is adjoined by a further circular-cylindrical section 13 which continues into a conical section 14 toward a longitudinal end 15 of the coupling element 10, which longitudinal end is remote from the main body. A diameter with respect to the cylinder axis G of the coupling element 10 is dimensioned so as to be smaller at every point than a smallest diameter of the main body 3.

The main body 3 has a recess 20 in a lower region. The recess 20 is open on the base side 4 and, on the base side 4, thus forms a removal opening 21 through which a fluid can enter into the recess 20 from the base side 4. On the lateral surface side, the recess 20 on the connecting surface 6 is likewise designed so as to be open such that a first valve opening 22 of a valve device 23 is produced. In the longitudinal direction, the recess 20 extends approximately over half of the length of the main body 3—in other words, it is therefore arranged in a lower half. In the transverse direction, the recess 20 extends virtually as far as the edges 8 and 9. Between edges 8 and 9 and recess 20, a narrow region of the connecting surface 6 extends downward in the longitudinal direction G in each case toward the base side 4. In said regions, a connecting section of a container wall (not illustrated in FIG. 1) can be fastened to the connecting surface 6 as far as the base surface 4. A front edge, in the longitudinal direction, of the valve opening 22 formed by the recess 20 is of rectilinear design and is oriented substantially perpendicularly to the longitudinal direction G.

A further recess 24 is formed arranged approximately centrally transversely with respect to the longitudinal direction G in an upper half of the connecting surface 6. The second recess 24 is open on the lateral surface side of the connecting surface 6 and forms a second valve opening 25 of the valve device 23. In the transverse direction, the recess 24 extends approximately over one fifth of the transverse size of the connecting surface 6, with the valve opening 25 being of substantially square design. An edge of the recess 24, which edge faces the recess 20, is of rectilinear design and is arranged substantially parallel to the front edge of the recess 20. Recesses 20 and 24 are spaced apart from each other in the direction of G in such a manner that the connecting surface 6 forms a narrow web 26 between the mutually facing edges of the valve openings 22 and 25. The valve openings 22 and 25 are therefore arranged adjacent on a common valve surface 6.1 which is formed by a region of the connecting surface 6.

A fluid channel 16 is formed in the longitudinal direction G in the coupling element 10, said fluid channel extending through the coupling element 10 and opening out at the longitudinal end 15 at a dispensing opening 17 and, at the opposite longitudinal end, adjoining a dispensing opening 2.1 of the closure piece 2. A dispensing channel 18 extends in the main body 3 from the dispensing opening 2.1 toward the removal opening 21. The dispensing channel 18 here comprises a dispensing section 18.1 which connects the dispensing opening 2.1 fluidically to the valve opening 26, and a removal section 18.2 which connects the valve opening 22 to the removal opening 21. In the present case, the removal section 18.2 is formed by the recess 20.

Figure 1C:
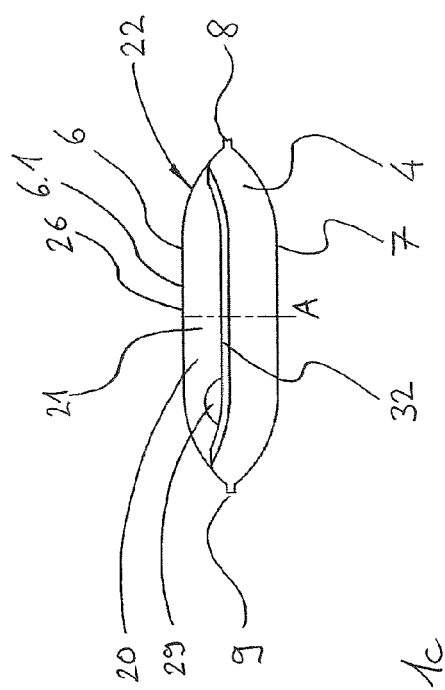

In a functionally ready state, the connecting surface 6 is covered by a flexible membrane 27 (indicated in FIG. 1d) which is not illustrated in FIGS. 1a-1c in order to provide better clarity. In particular, the membrane 27 covers the valve openings 22 and 25 and is fastened to the connecting surface 6 in such a manner that said membrane is raisable from the connecting surface 6 in the region of the web 26. If the membrane bears against the web 26 in a fluid-tight manner, a fluid cannot pass from the recess 20 to the recess 24. If, by contrast, the membrane 27 is raised from the web 26, a fluid channel is formed between web 26 and membrane 27, said fluid channel communicating with the valve openings 22 and 25 and therefore permitting fluid to pass between the recesses 20 and 24. The membrane 27 here is raisable from the web 26 preferably in a region which has approximately a transverse size which corresponds to the transverse size of the recess 24 and reaches as far as the mutually facing edges of the valve openings 22 and 25. The flexible membrane 27 is fixedly connected to the connecting surface 6 at least in the adjacent regions of the connecting surface 6, in particular as far as the valve openings 22 and 25.

A further recess 28 is formed within the recess 20, said recess 28 being arranged offset laterally with respect to the cylinder axis G and reaching as far as a front boundary of the recess 20. The recess 28 is open toward the recess 20, and therefore the recesses 20 and 28 communicate with each other.

A further fluid channel 29 is formed on the main body 3 parallel to the longitudinal axis G, said fluid channel being open on the end side 5 at a connecting opening 30 and extending in the main body 3 as far as the recess 28 and opening out there. The fluid channel 29 is designed so as to taper conically toward the recess 28 (see FIG. 1b), and therefore a corresponding cone of a fluid source can be connected in order to fill a container provided with the closure piece 2. In the embodiment illustrated, a fluid fed via the fluid channel 29 passes via the recess 28 into the recess 20 and from there via the opening 21 into a container connected to the closure piece 2. The removal opening 21 therefore at the same time forms a filling opening via which the container can be filled via the connecting opening 30. The system of fluid channel 29, recess 28 and recess 20 therefore acts as a filling channel of the closure piece 2.

FIG. 1b shows a lateral top view of the closure piece 2 according to FIG. 1a in the direction of the connecting surface 6, wherein concealed structures are indicated by dashed lines.

As is revealed in FIG. 1b, a corresponding blind hole 31 is formed on the end side 5 opposite the connecting opening 30 with respect to the cylinder axis G. The blind hole 31 here is formed substantially analogously to the fluid channel 29, but ends in the longitudinal direction at a distance from a front boundary of the recess 20. The blind hole 31 here serves to receive a closure pin, which is not required, of a connecting cap provided for closing the connecting opening 30 (see below, for example FIGS. 2a-2c). FIG. 1b shows two sectional surfaces A and B, of which the plane A comprises the longitudinal axis G and is perpendicular to the connecting surface 6, and the plane B is arranged parallel to the plane A in the region of the fluid channel 29. The corresponding sectional figures are illustrated in FIGS. 1e and 1f.

FIG. 1c shows a top view of the base side 4 of the closure piece 2. A rib 32 is arranged within the recess 20 in the vicinity of the base side 4. The rib 32 here serves as a pinching-off rib 32 onto which the flexible membrane 27 can be mechanically pressed from the outside after the filling of the container 38 until the fluid channel 29 is closed by a closure pin 64 or 65 of the connecting cap 50.

FIG. 1d shows a top view of the end side 5 of the closure piece 2, wherein concealed structures are indicated by dashed lines. Container walls 33 and 34 are indicated on the connecting surfaces 6 and 7, said container walls being fastened on the connecting surfaces 6 and 7 by connecting sections 35 and 36. The connecting section 35 is of flexible design in the region of the valve openings 22 and 25 and of the web 26 and, in said regions, forms the abovementioned flexible membrane 27 of the valve device 23. In particular, the connecting section 35 is raisable from the connecting surface 6 in the region of the web 26.

FIG. 1e shows a longitudinal section through the closure piece 2 in the plane A. The fluid channel 16 of the coupling element 10 extends from the longitudinal end 15 as far as the recess 24 and is open over the entire cross section thereof at the longitudinal end 15 (dispensing opening 17) and at the recess 24. For this purpose, the recess 24 extends into the main body 3 to a corresponding depth. In this connection, "depth" refers to a size in the direction transversely with respect to the cylinder axis G parallel to the plane A, i.e. substantially perpendicularly to the connecting surfaces 6 and 7. As emerges from FIG. 1e, the recess 20 extends in the region of the plane A in a direction transversely with respect to the cylinder axis G into the main body 3 up to a depth which substantially corresponds to the position of the longitudinal axis G. The depth of the recess 20 can be matched in each case to the specific requirements. For example, the dead volume of the recess 20 can be reduced by reducing said depth.

FIG. 1f shows a longitudinal section through the closure piece 2 in the plane B. The fluid channel 29 tapers conically from the connecting opening 30 on the end side 5 toward the recess 28. On the end side 5, the fluid channel 29 is open over the entire cross section thereof at the connecting opening 30. The fluid channel 29 has a narrow section 30.1 of cylindrical design at the connecting opening 30.

In the region of the plane B, the recess 20 extends in a direction transversely with respect to the cylinder axis G substantially as far as the position of the axis G. The recess 28 is designed and dimensioned as a depression in the recess 20 in such a manner that the fluid channel 29 is open over the entire cross section thereof. Front boundary walls of the recesses 20 and 28 here coincide, wherein the recess-side opening of the fluid channel 29 is formed on the front boundary wall. The recesses 24 and 28 have substantially the same depth.

FIG. 2a shows an outer oblique view of a connecting cap 50 for a device 1 according to the invention, in particular for attaching to the closure piece 2. The connecting cap 50 has a main body 51 which is of substantially circular-cylindrical design and has a cylinder axis H. Two webs 53 and 54 which are arranged in the direction of the axis H and in a plane C and which extend over the entire length of the main body 51 are formed opposite each other with respect to the cylinder axis H on a lateral area 52 of the main body 51. When the device 1 is placed into a dispensing device, the webs 53 and 54 predetermine an orientation of the connecting cap 50.

A base surface 55 of the main body 51 is provided and designed for attaching to the closure piece 2 (see FIGS. 3a-3c). At a transition from the base surface 55 onto the lateral area 52, the closure cap 50 has two closure means 56 and 57 which are arranged opposite each other with respect to the cylinder axis H and in a plane D arranged perpendicularly to the plane C. The closure means 56 and 57 are designed in the manner of a segment of a circular cylinder and are integrally formed in an articulated manner by a tip on the main body 51 of the connecting cap 50 in such a manner that said closure means can be pivoted toward the longitudinal axis. In the illustration of FIG. 2a, the closure means 56 and 57 are in a standby position and project laterally with respect to the cylinder axis H. The closure means 56 and 57 serve, inter alia, for blocking the valve device 23 in a storage or transport state of the device 1 and are described in more detail in FIGS. 3a-3d.

The main body 51 has a cavity 58 which is open forward on an end side 59 opposite the base surface 55. A thread 60 is formed on an inner wall of the cavity 58. The cavity 58 contains a cone 61 which is oriented in the longitudinal direction H and, at a front longitudinal end, has a dispensing opening 62 which communicates with a fluid channel 63 formed in the cone 61.

Cavity 58 together with the thread 60 and the cone 61, as coupling means 72 of the connecting cap 50, form parts of a known Luer lock connection. The dimensions of the parts are selected according to the known standardized standards, and therefore the connecting cap 50 can be coupled to correspondingly standardized, complementary connections.

Two closure pins 64 and 65 which extend away from the base surface 55 in the direction of H are formed opposite each other with respect to the cylinder axis H on the base surface 55 (see, for example, FIG. 2b). The closure pins 64 and 65 are designed as truncated cones which converge conically away from the base surface 55 and are dimensioned in such a manner that they can each be introduced into the fluid channel 29 or into the blind hole 31 on the end side 5 of the closure piece 2. Fluid channel 29 and blind hole 31 here are dimensioned in relation to the pins 64 and 65 in such a manner that an interlocking connection in the manner of a cone coupling arises when the pins 64 and 65 are completely arranged in the fluid channel 29 or blind hole 31. The closure pins 64 and 65 thus permit a fluid-tight closing-off of the fluid channel 29 when the closure cap 50 is attached to the closure piece 2. By two pins 64 and 65 being arranged symmetrically with respect to the cylinder axis H, the connecting cap 50 can be attached to the closure piece 2 in two alignments, wherein in each case one of the connecting pins 64 and 65 is arranged in the fluid channel 29 and the other is arranged in the blind hole 31.

FIG. 2b shows a longitudinal section of the connecting cap 50 in the plane C while FIG. 2c shows on an enlarged scale a detail which is indicated by a circle in FIG. 2b. The fluid channel 63 arranged in the cone 61 extends from the dispensing opening 62 arranged at the front longitudinal end toward the base surface 55 of the connecting cap 50. Following the fluid channel, a receiving space 66 is formed in the cone 61, said receiving space being open in the longitudinal direction H at an access opening 67 on the base surface 55. The fluid channel 63 is open toward the receiving space 66, and therefore receiving space 66 and fluid channel 63 communicate with each other. The receiving space 66 is of complementary design to the coupling element 10 of the closure piece 2, and therefore said coupling element can be introduced into the receiving space 66 through the access opening 67.

An inner wall of the receiving space 66 has sections corresponding to the sections 11 to 14 of the coupling element 10, in particular an annular groove 68 in which the annular bead 12 of the coupling element 10 is latched when said coupling element is arranged in the receiving space 66. Toward the fluid channel 63, the receiving space 66 has a conically tapering section 69 with which the conical section 14 of the coupling element 10 ensures a fluid-tight seat in the manner of a cone coupling when the coupling element 10 is arranged in the receiving space 66.

FIG. 3a shows a schematic longitudinal cross section through a dispensing device 80 for the manual dispensing of a fluid 39 from the device 1. The dispensing device 80 is in a state before a storage or transport state is produced. A housing 82 of the dispensing device 80 has an elongate receiving space 83 in which the device 1 according to the invention with an attached connecting cap 50 is arranged. The connecting cap 50 here is attached to the closure piece 2 in such a manner that the axes G and H are arranged coaxially. The receiving space 83 is forwardly open in the longitudinal direction at a dispensing-side longitudinal end. The device 1 is arranged in the receiving space 83 in such a manner that the connecting cap 50 protrudes forward out of the receiving space 83 at least with the coupling means, which is designed as a Luer lock. The container walls 33 and 34 form an elongate, bag-like container 38 which is arranged in the longitudinal direction of the dispensing device 80. An interior space in the container 38 is substantially completely filled with the fluid 39 provided for dispensing. For the mounting of the container 38 or of the device 1 in the receiving space 83, lateral sections of the container walls 33 and 34 can be fastened to the housing 82, for example can be clamped by housing halves and can advantageously be welded thereto (not illustrated).

At a longitudinal end opposite the dispensing-side longitudinal end of the main body 82, a plunger 84 which is designed in the manner of a piston is arranged in such a manner that said plunger can be pushed from the outside, for example by a user, from the rear into the receiving space 83. The plunger 84 has a longitudinal gap 85 which is open toward the receiving space 83 and extends substantially over the entire length of the plunger 84. A rear end fold 40 of the container 38 is arranged in a frontmost region of the gap 85. In the position of FIG. 3a, the plunger 84 is completely extended out of the receiving space 83.

The closure means 56 and 57 of the connecting cap 50 are completely unfolded laterally in the standby position, analogously to the illustration of FIG. 2a. A closure cap 81 is provided for attaching to and sealing the dispensing region of the dispensing device 80.

FIG. 3b shows the dispensing device 80 with an attached closure cap 81 in a transport or storage state. The closure cap 81 here is pulled from the front over the connecting cap 50 and is fastened releasably, for example welded, for example via a predetermined breaking point 81.1, to the housing 82 of the dispensing device 80. The closure cap 81 here completely spans the connecting cap 50 and the dispensing region and seals the latter, in particular in a sterile manner, against contamination with dirt or germs. Prior to use, the closure cap 81 has to be removed, with the predetermined breaking point, which is designed, for example, as a dirt seal, having to be broken.

The closure cap 81 is dimensioned in such a manner that, when said closure cap is attached, the closure means 56 and 57 of the connecting cap 50 are folded inwards from an inner wall 81.2 of the closure cap 81, toward the cylinder axis H. In particular, the closure means 56 and 57 are pivoted into an active position. In the process, press-on sections 70 and 71 which are formed on the respective closure means 56 and 57 in the region of a longitudinal position of the web 26 are pivoted onto the closure piece 2 and pressed against the latter. The closure means 56 which is arranged on the side of the valve openings 22 and 25 is pressed here by the press-on section 70 thereof in the region of the web 26 between the valve openings 22 and 25 onto the flexible membrane 27. The flexible membrane 27 is thereby clamped between press-on section 70 and valve surface 6.1, and therefore the closure means 56 is in a closed position and blocks the valve device 23 in the closed position thereof. The required press-on pressure of the closure means 56 is maintained by the closure cap 81 which blocks the closure means 56 from raising from the closure piece 2.

The further closure means 57 is pressed against the closure piece 2 on the side of the connecting surface 7 and thus supports the closure piece 2 on the closure cap 81. If the connecting cap were attached rotated through 180° about the cylinder axis H to the closure piece 2, which would readily be possible owing to the symmetrical design of the connecting cap 50, the functions of the closure means 56 and 57 would be interchanged.

FIG. 3c shows the dispensing device 80 in a dispensing-ready state in which the closure cap 81 has been removed. The closure means 56 and 57 continue to be in an active position in which said closure means are lowered by the press-on sections 70 and 71 onto the closure piece 2 and onto the connecting sections of the container walls 33 and 34. However, because the closure cap 81 is absent, the closure means 56 and 57 can be pivoted away from the closure piece 2 and are therefore in a release position. In particular, in the release position, the flexible membrane 27 can therefore be raised from the valve surface 6.1 in the region of the web 26, and therefore the valve device 23 can be brought into the open position.

FIG. 3d shows the dispensing device 80 in a partially emptied state, i.e. in which part of the fluid 39 has been dispensed from the container 83 of the device 1. For this purpose, the plunger 84 has been pushed forwards into the receiving space 83, as a result of which the gap 85 is pushed over the container 38. The container walls 33 and 34 are compressed here in the gap 85, as a result of which a positive pressure is generated in the fluid 39 in the interior space in the container 38. When a threshold value which is predetermined by the valve device 23 is exceeded, and depending on the pressure of the closure means 56 in the release position, the valve device 23 moves into the open position by raising of the membrane 27 in the event of a sufficient positive pressure such that the fluid 39 passes through the removal opening 21 into the recess 20 and from there via the valve device 23 and the fluid channel 16 and via the dispensing opening 17 into the fluid channel 63 of the connecting cap 50 where said fluid is conducted to the dispensing opening 62.

FIGS. 4a to 4c show a further possible embodiment of a closure piece 102 for a device according to the invention. FIGS. 4a and 4b show longitudinal sections through the closure piece 102, wherein a connecting cap 150 is attached in FIG. 4b. FIG. 4c shows an outer oblique view of the closure piece 102 with an attached connecting cap 150. FIGS. 4a to 4c are jointly described below.

The closure piece 102 comprises a main body 103 with a cylindrical connecting section 103.1 having a lenticular base surface 104 and a cylindrical section 103.2 adjoining the latter in a longitudinal direction J and having an elliptical cross section. A peripheral groove 103.3 with which the closure piece 102 can be inserted in a correspondingly designed dispensing device (not shown) is arranged between the sections 103.1 and 103.2.

The connecting section 103.1 has two connecting surfaces 106 and 107 which respectively converge transversely with respect to the longitudinal direction J at a common edge 108 and 109 and which are provided for the fastening of connecting sections of container walls (not illustrated).

Valve openings 120.1/2 and 122.1/2, which are adjacent in a paired manner, of respective valve devices 123.1 and 123.2 are arranged on a lateral area of the cylindrical section 103.2. The valve openings 120.1/2 of the valve device 123.1 here are arranged opposite the valve openings 122.1/2 of the valve device 123.2 with respect to the longitudinal axis J.

The main body 103 contains a fluid channel 116 which is designed as a dispensing channel and has a first section 116.1 which fluidically connects a removal opening 121 arranged on the base surface 104 to the valve opening 120.1 of the valve device 123.1. A second section 116.2 of the fluid channel 116 continues from the adjacent valve opening 120.2 in the longitudinal direction J through a coupling element 110, which is integrally formed on an end side 105 of the cylindrical section 103.2 and is designed as a cone, as far as a dispensing opening 117.

The main body 103 contains a further fluid channel 129 which is designed as a filling channel and has a first section 129.1 which fluidically connects a filling opening 121.1 arranged on the base surface 104 to the valve opening 122.1 of the valve device 123.2. A second section 129.2 of the fluid channel 129 continues forward from the adjacent valve opening 122.2 as far as a connecting opening 130 formed on the end side 105 of the cylindrical section 103.2.

The cylindrical section 103.2 is surrounded by an elastic membrane 127 which is of sleeve-like design, in particular covers the valve openings 120.1/2 and 122.1/2 and bears in a fluid-tight manner against the lateral area of the cylindrical section 103.2. The elastic membrane 127 simultaneously acts here as a flexible membrane for the two valve devices 123.1 and 123.2.

In FIG. 4b, a connecting cap 150 is attached to the cylindrical section 103.2 and presses the membrane 127 against the lateral area. In the region of the valve device 123.1, a cutout is formed in the connecting cap 150 such that, in this region, the membrane 127 is raisable from the lateral area even with the connecting cap 150 attached. The valve device 123.2 is therefore blocked in the closed position when the connecting cap 150 is attached, while the valve device 123.1 can be brought into the open position by raising of the membrane 127 even when the connecting cap 150 is attached. For the filling operation, the connecting cap 150 is not attached to the closure piece 102, and therefore a connected container can be filled via the filling channel 129 via the valve device 123.2. After the filling, the connecting cap 150 is attached, as a result of which the filling channel 129 is blocked, i.e. the valve device 123.2 is blocked in the closed position. In the process, a closure pin 164 of the connecting cap 150 enters the section 129.2 and closes the latter in a fluid-tight manner on the end side 105.

Figure 5:
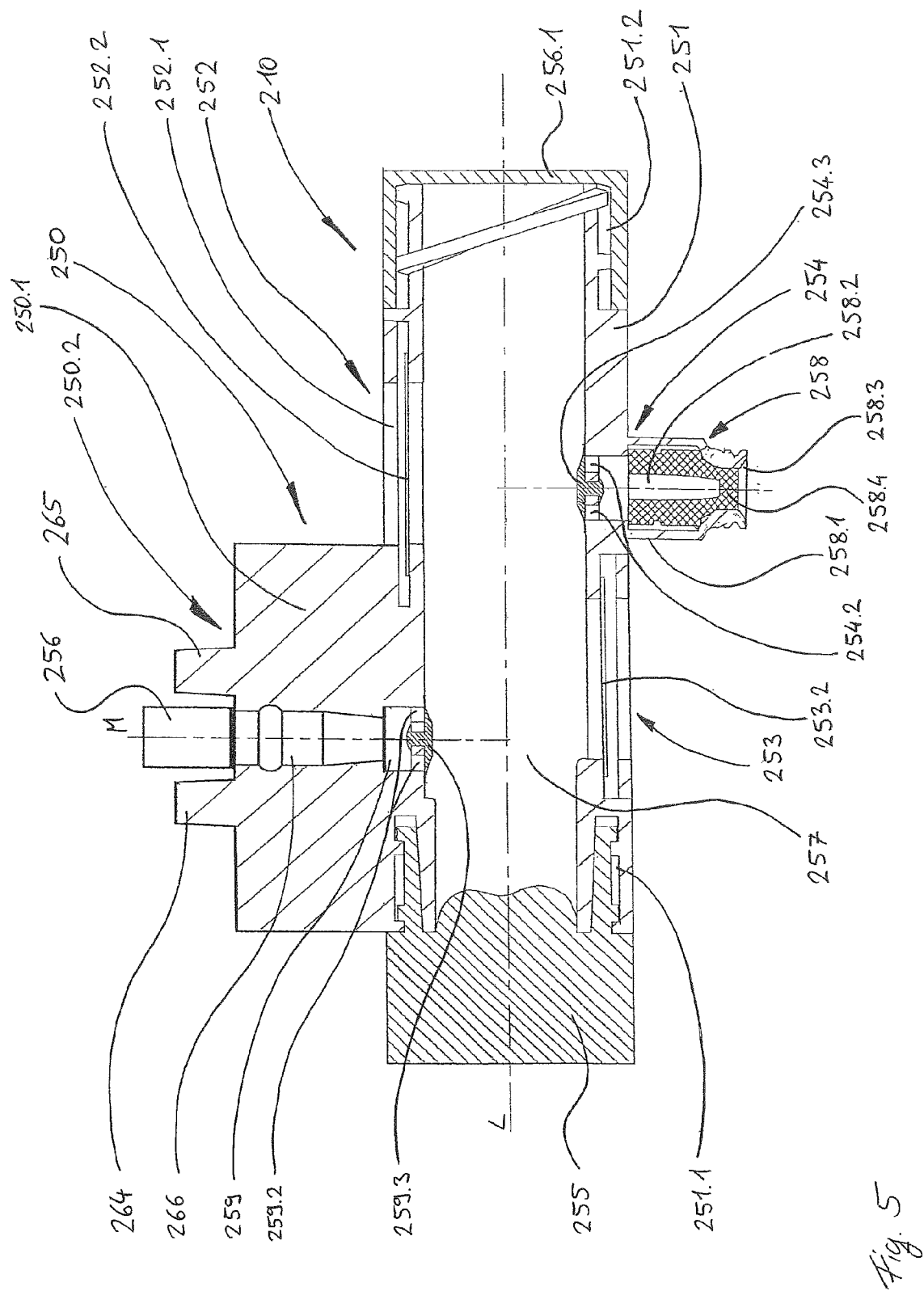
FIG. 5 shows a sectional view in the longitudinal direction through a further embodiment of a closure cap with a tubular coupling means.

FIG. 5 shows a further embodiment of a connecting cap 250 for the closure piece 2 with a coupling means 210 for connecting to a fluid-conducting system, in particular for use in the sphere of dialysis systems. The coupling means 210 is designed as an elongate tube section 251 and is integrally formed directly on a main body 250.1, which is of substantially circular-cylindrical design, of the connecting cap 250. A longitudinal direction L of the tube section 251 is arranged substantially perpendicularly to a cylinder axis M of the main body 250.1. A connecting region 250.2 of the connecting cap 250 for the connection of a device 1 according to the invention comprises a receiving space 266 for the coupling element 10 of the closure piece 2, a closure means 256 and two closure pins 264 and 265 which substantially correspond in shape and function to the similar elements described, for example, in FIGS. 2 to 3.

The end sides of the tube section 251 are respectively provided with a coupling point 251.1 and 251.2 which permits connection of the tube section 251 to the fluid-conducting system (not illustrated). In the illustration in FIG. 5, the coupling point 251.1 is designed as a snap-type coupling and is provided with a corresponding removable closure cap 255. The coupling point 251.2 is designed as a threaded coupling and likewise has a removable closure cap 256.1.

The receiving space 266 opens out directly into an access opening 259 of the tube section 251. On the inner side of the tube wall, the access opening 259 has a plurality of openings 259.2 which permit passage of liquid out of the receiving space 266 into an interior space 257 in the tube section 251. The openings 259.2 here are preferably arranged annularly around a centrally arranged fastening point of a screen valve 259.3. A screen of the screen valve 259.3 extends into the interior space 257 and is designed in such a manner that it completely covers the openings 259.2. The screen is preferably designed as a thin sealing lip which, nestling against the inner side of the tube wall, tapers radially outward from the fastening point. At a border of the screen, the latter therefore bears substantially steplessly against the inner wall of the tube section 251.

If a fluid is then dispensed from a connected device 1 according to the invention (not illustrated in FIG. 5), the fluid enters the access opening 259. If a pressure in the fluid is of a sufficient size, the screen of the screen valve 259.3 is raised from the inner wall of the tube, and therefore the openings 259.2 are released and the fluid enters the interior space 257. As soon as there is no more pressure in the fluid, the screen valve 259.3 closes by the screen being placed again against the inner wall of the tube over the openings 259.2 in a sealing manner.

By means of the substantially smooth transition from the tube wall to the screen, the overall result is only a minor adverse effect on a fluid of the fluid-conducting system flowing in the interior space 257 in the tube section 251. It is also immediately apparent that, because of the construction according to the invention, the interior space 257 does not contain any dead spaces in which the flowing liquid could undesirably reside.

In addition, the coupling means 210 has three injection ports 252 to 254. An injection port 252 formed directly next to the main body 250.1 comprises a septum 252.2 which is inserted into an opening 252.1 of the tube wall. The septum 252.2 permits a self-closing penetration by means of, for example, an injection needle. The septum 252.2 is formed in the tube wall in such a manner that the septum forms a substantially direct continuation of the tube wall and thus as far as possible does not obstruct or swirl a flowing liquid. For this purpose, the septum 252.2 is fastened directly to the tube wall, for example is welded thereto by ultrasound or laser. A further injection port 253 is formed in the tube wall opposite the access opening 259 with respect to the longitudinal axis L. The injection port 253 is formed substantially analogously to the injection port 252 and comprises a septum 253.2.

A further injection port 254 is formed in the tube wall opposite the injection port 252 with respect to the longitudinal axis M. Said further injection port 254 has openings 254.2 analogous to the access opening 259, and a screen valve 254.3. However, in contrast to the access opening 259, a coupling means 258 is provided on the outer side of the tube section 251, said coupling means permitting a needle-free coupling of a medicinal device for dispensing fluid. In the illustration of FIG. 5, the coupling means 258 is designed as what is referred to as a swabable valve. Valves of this type comprise a coupling base 258.1 which, in the present case, is integrally formed on the tube section. An interior space 258.2 in the base 258.1, which interior space communicates with the openings 254.2, has a connecting opening 258.3 with, for example, an inner cone of a Luer coupling. In order to provide a seal against dirt or contamination, the interior space contains a slot valve 258.4 which is pushed back when an outer cone is introduced and, when the latter is removed, closes the outer opening 258.3 again. The slot valve 258.4 is arranged in the opening 258.3 in such a manner that said slot valve can be easily swabbed, i.e. cleaned, from the outside. Couplings of this type are described in U.S. Pat. No. 6,651,956 (Halkey-Roberts Corporation). FIG. 5 is understood as a schematic view, and therefore a size ratio, for example between the connecting cap 250 and coupling means 258, does not have to correspond to the actual ratio.

It goes without saying that the tube section 251 can also be integrated, for example, directly into a tube or a hose. Similarly, the tube section can be fixedly closed, for example, on one side and can only be provided at one end for coupling to a fluid-conducting system. Similarly, it is immediately apparent that other or additional coupling means, such as, for example, further Luer locks and also additional injection ports, can also be provided. In general, it is recommended that, in addition to the possibility for the coupling of a device according to the invention, the tube section has at least one further port to which a further dispensing device, optionally also of a different type, such as, for example, a syringe, can be coupled.

It is immediately clear from FIG. 5 that the coupling element 210 can also be integrally formed directly on a closure piece of a device according to the invention. In this case, the main body 3 of the closure piece 2 can be connected, for example by the end side 5 thereof, directly to the tube section 251, for example can be integrally formed thereon in one piece, with the valve opening 25 directly communicating with the access opening 259 via a fluid channel.

Figure 6A:
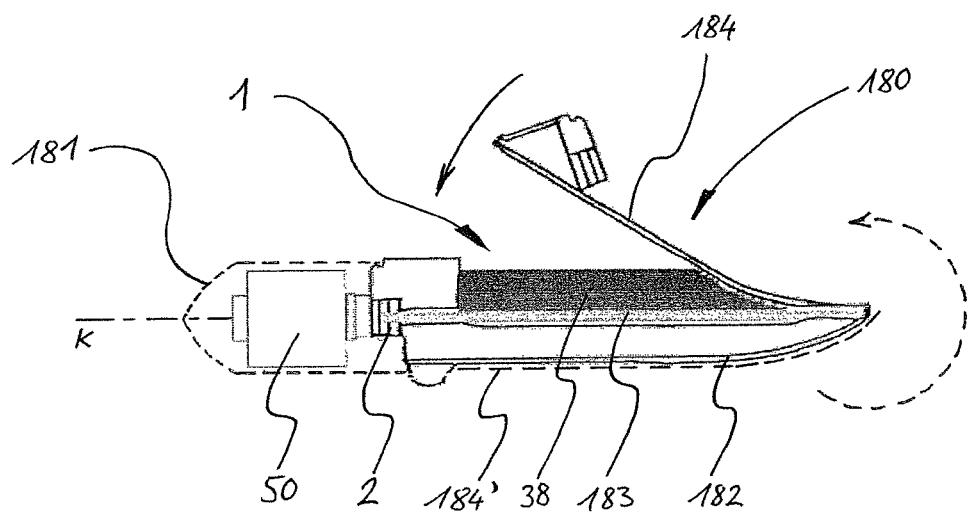
FIG. 6a shows a view of a further embodiment of a dispensing device with a device according to the invention for receiving and dispensing a fluid arranged therein.

FIG. 6a shows a schematic view of a further embodiment of a dispensing device 180 for the manual dispensing of a fluid 39 from the device 1. The dispensing device 180 is particularly suitable, for example, for the dispensing and application of a disinfectant. However, said dispensing device is also particularly suitable, for example, for use with cosmetic fluids or in the foodstuff sphere, for example for viscous foodstuffs, such as sauces (ketchup, mustard, etc.).

A housing 182 of the dispensing device 180 has an elongate receiving space 183 in which the device 1 according to the invention with an attached connecting cap 50 is arranged. In the figure of FIG. 6a, the connecting cap 50 is only indicated schematically without any detailing. The receiving space 183 is forwardly open in a longitudinal direction K at a dispensing-side longitudinal end. The device 1 is arranged in the receiving space 183 in such a manner that the closure piece 2 protrudes forward together with the connecting cap 50 out of the receiving space 183.

The housing 182 is designed so as to be substantially open on half a side transversely with respect to the longitudinal direction K such that pressure can be directly exerted on the container 38 from the side. At a longitudinal end opposite the dispensing-side longitudinal end of the main body 182, i.e. at a rear longitudinal end, a lever arm 184 which is designed as a pusher is articulated pivotably about a pivot axis arranged transversely with respect to the longitudinal axis K. The pusher 184 here is arranged on the housing 182 in such a manner that said pusher can be pivoted from the open half into the receiving space 183 (solid arrow). The pusher 184 is designed corresponding to an outer shape of the housing 182, and therefore said pusher, in a storage or transport state, can be folded onto the outer side of the housing 182 and can be latched there if the need arises (position 184', indicated by dashed lines). The pusher 184 is unfolded for use (dashed arrow).

In the storage or transport state, the dispensing region of the dispensing device 180 is provided with a closure cap 181 and is sealed, wherein the closure cap 181 fixes the closure means 56 and 57 of the connecting cap 50 analogously to the illustration of FIG. 3b.

Figure 6B:
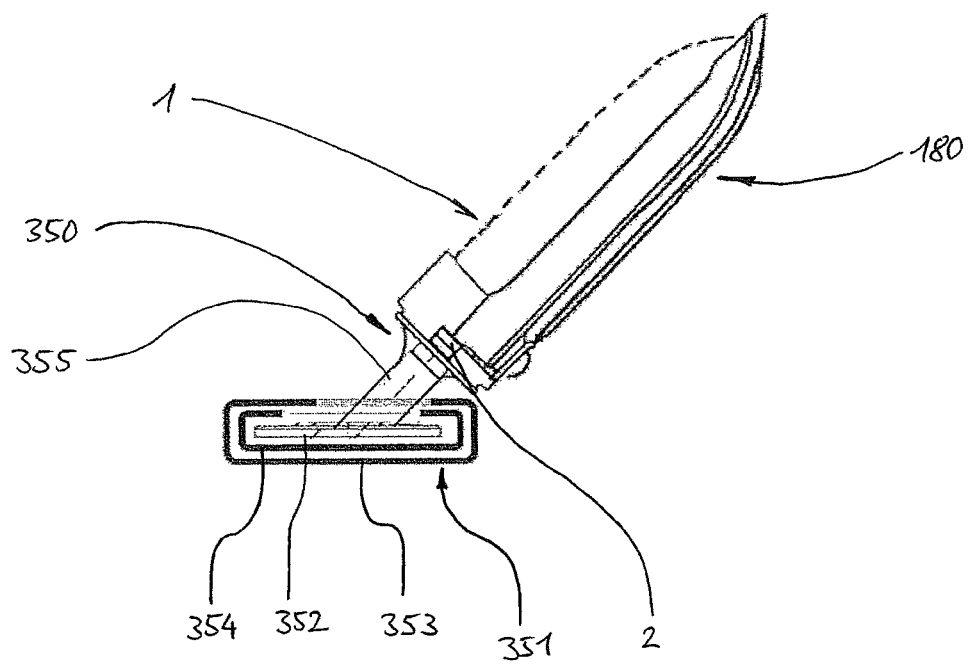
FIG. 6b shows a view of the dispensing device according to FIG. 6a with a connecting cap with an application means.

The dispensing device 180 is particularly advantageous in particular also in conjunction with a connecting cap 350 with an application means 351, such as, for example, a sponge 352, if the fluid 39 comprises, for example, a disinfectant for two-dimensional application. FIG. 6b shows schematically an embodiment of this type. For this purpose, the connecting cap 350 has a holder 355 for the application means 351, said holder having a fluid channel (not illustrated) which is located on the inside and communicates with the dispensing opening of the closure piece 2. The fluid channel opens out on the application means 351, and therefore the latter can be directly supplied with the fluid 39 from the device 1 according to the invention.

Owing to the arrangement of the pusher 184 (in a transport or storage position in FIG. 6b), the dispensing device 180 can be operated in a simple manner with the thumb by the user as the user brushes over the region to be disinfected with the application means 351, which is impregnated with the disinfectant on account of the actuation. The application means 351 here comprises the sponge 352 which, in the present case, is encased by two layers 353 and 354, for example, of a fleece, mesh or microfilter. The individual layers 353 and 354 are designed to be removable, and therefore, after rough cleaning, an outermost layer 353 can be removed in order to carry out fine cleaning with the further layer 354 which is still clean. For the final disinfection, the further layer 354 can also be removed, and therefore the final disinfection can be carried out with the sponge 352 which is still clean.

FIG. 7*a* shows an outer oblique view of a further embodiment of a closure piece 2' for a device according to the invention. The closure piece 2' substantially corresponds to the closure piece 2 (FIGS. 1*a*-1*f*) and therefore reference is substantially made below only to different embodiments. Corresponding parts bear the same reference number as in FIGS. 1*a*-1*f*, the reference number being provided with a prime.

In contrast to the closure piece 2, the main body 3' of the closure piece 2' is not of cylindrical design. The main body 3' converges conically downward in cross section from a substantially lenticular end surface 5'. Two connecting surfaces 6' and 7' of the main body 3', which connecting surfaces are formed on the lateral surface side, converge here substantially at a common lower edge 4'. The connecting surfaces 6' and 7' each have centrally a respective convex curvature 6.1' and 7.1', and therefore the main body 3' has a substantially constant thickness substantially over the entire length in a central region (see FIGS. 7*c* and 7*d*). Toward the edge 4', the curvatures 6.1' and 7.1' converge with a comparatively steep slope. Laterally, the connecting surfaces converge at common edges 8' and 9' which are designed as longitudinal webs.

On the end side 5', a coupling element 10' which is designed analogously to the coupling element 10 and extends away from the end side 5' along the cylinder axis G' is formed on the main body 3'.

In the region of the curvature 6.1', the main body 3 has a recess 20' in a lower region. The recess 20' is open at the edge 4' in the beveled region of the curvature 6.1' and thus forms a removal opening 21'. On the lateral surface side, the recess 20' is likewise designed to be open on the connecting surface 6'. In the transverse direction, the recess 20' extends only in the region of the curvature 6.1'. Between edges 8' and 9' and recess 20', the connecting surface 6' forms connecting regions 6.2' and 6.3' which are two-dimensional in the longitudinal direction G' and extend from the end side 5' as far as the edge 4'. A container wall can be fastened two-dimensionally in said connecting regions 6.2' and 6.3'.

A further recess 24' is formed in the region of the curvature 6.1' above the recess 20', i.e. closer to the end side 5'. The second recess 24' is open on the lateral surface side at the connecting surface 6'. Recesses 20' and 24' are spaced apart from each other in the direction of G' in such a manner that the connecting surface 6' forms a narrow web 26' between the recesses 20' and 24'.

A further recess 28' which is arranged offset laterally with respect to the cylinder axis G' is formed in the recess 20'. Analogously to the closure piece 2, the closure piece 2' has a fluid channel 16' in the coupling means 10' and a fluid channel 29' in the main body 3', said fluid channels opening out in the respective recesses 24' and 28'. The fluid channel 29' opens out on the end side 5' and is open at a connecting opening 30' whereas the fluid channel 16' is open at a dispensing opening 17' of the coupling means 10'. Analogously to the closure piece 2, a blind hole 31' is formed on the end side 5' opposite the connecting opening 30' with respect to the cylinder axis G'.

In the functionally ready state, the connecting surface 6' is covered at least in the region of the recesses 20' and 24' by a flexible membrane (not illustrated). Recesses 20' and 24' therefore form valve openings of a valve device of the closure piece 2'. In a region at the edge 4', a rib 32' is produced by the connecting surfaces 6' and 7' converging conically at the recess 20'. The rib 32' serves as a pinching-off rib 32' onto which the flexible membrane can be pressed mechanically from the outside, for example after the filling of a container connected to the closure piece 2', until the fluid channel 29' is closed, for example, by a closure pin.

On the end side 5', the closure piece 2' has stop plates 5.1' and 5.2' formed substantially semicircularly on both sides of the coupling means 10'. Said stop plates extend perpendicularly to the longitudinal direction G' and, for the defined positioning, can serve here as a stop for a supporting structure (see further below), such as, for example, a supporting frame or a dispensing device. On the other hand, the stop plates 5.1' and 5.2' can also serve as mounting means of the closure piece 2', for example for mounting in a dispensing device or for handling during the production or filling of a device according to the invention provided with the closure piece 2'. Mounting pins 5.3' and 5.4' in each case extend forward in the longitudinal direction G' from the stop plates 5.1' and 5.2'. The mounting pins 5.3' and 5.4' have different lengths, and therefore, during the handling, an orientation about the longitudinal axis G' of the closure piece 2' can be identified, for example, visually or mechanically. In addition, the mounting pins 5.3' and 5.4' serve as guide means or mounting means for a correspondingly designed closure cap 50' (see FIG. 8).

FIG. 7*b* shows a lateral exterior view of the closure piece 2'. FIG. 7*b* shows two sectional surfaces A' and B', the corresponding sectional depictions of which are illustrated in FIGS. 7*c* and 7*d*. Sectional plane A' comprises the longitudinal axis G' while the sectional plane runs parallel to the plane A' in the region of the fluid channel 29'. The sectional planes A' and B' are substantially perpendicular to the connecting surfaces 6' and 7'.

FIG. 8 shows an outer oblique view of a further embodiment of a connecting cap 50'. The connecting cap 50' substantially corresponds to the connecting cap 50 (FIGS. 2*a*-2*c*), and therefore reference is made below essentially only to different embodiments. Corresponding parts bear the same reference number as in FIGS. 2*a*-2*c*, said reference number being provided with a prime.

In contrast to the connecting cap 50, the connecting cap 50' has holding means 53' and 54' arranged instead of the webs 53 and 54 in the plane C'. The holding means 53' and 54' are designed as half tube sections which are open on the end side and have a C-shaped cross section. The tube sections are integrally formed in the longitudinal direction H' along a surface line with a back of the C shape on a main body 51' of the connecting cap 50'. A cross section of the tube sections is dimensioned in such a manner that the mounting pins 5.3' and 5.4' of the closure piece 2' can be introduced into the interior space. The connecting cap 50' is dimensioned in such a manner that, when the connecting cap 50' is attached to the closure piece 2', the mounting pins 5.3' and 5.4' are automatically introduced into the interior space of in each case one of the holding means 53' and 54'. The holding means 53' and 54' here prevent the connecting cap 50' from being able to be attached in a non-designated orientation.

Figure 9A:
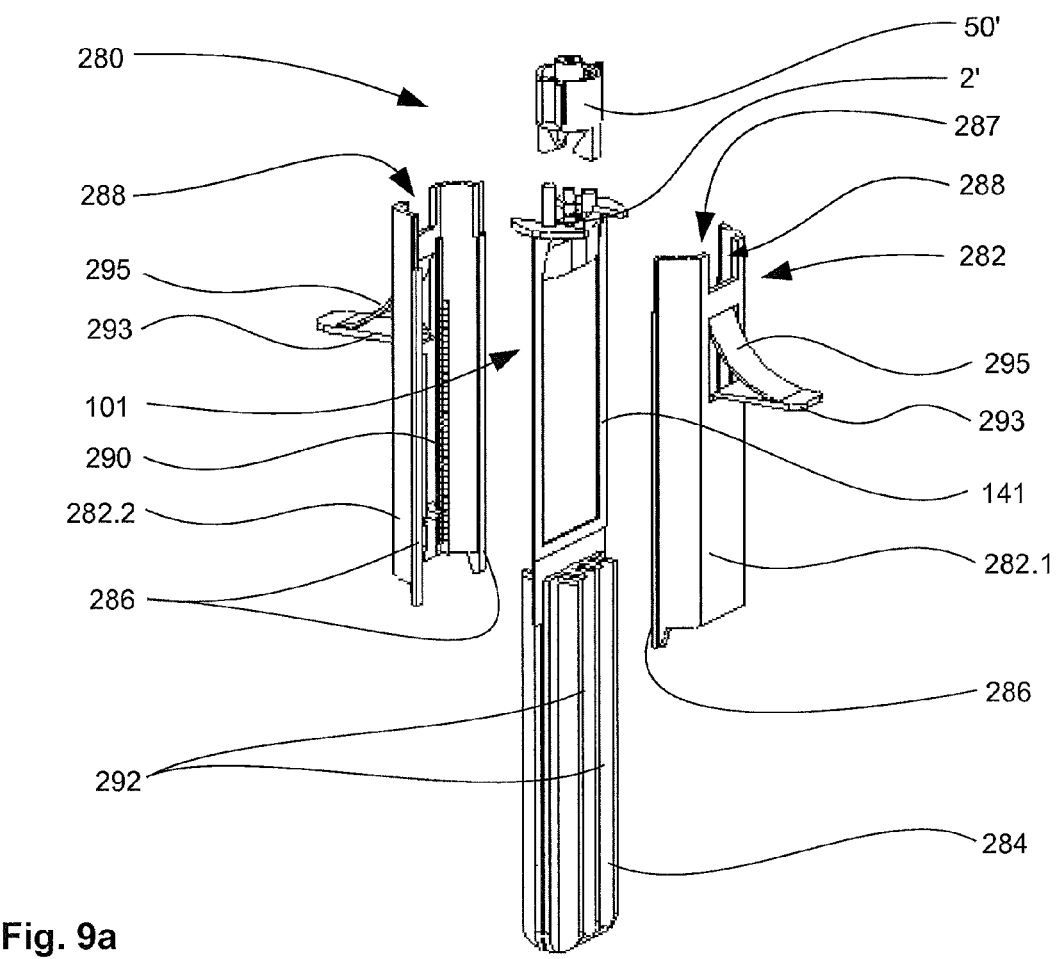
FIG. 9a shows an exploded illustration of a further embodiment of a dispensing device.

FIG. 9*a* shows an exploded illustration of a further embodiment of a dispensing device 280 for the manual dispensing of a fluid from a device 101 according to the invention having a closure piece 2'. The dispensing device 280 substantially corresponds in a functional respect to the dispensing device 80 illustrated in FIGS. 3*a*-3*d*.

Figure 9B:
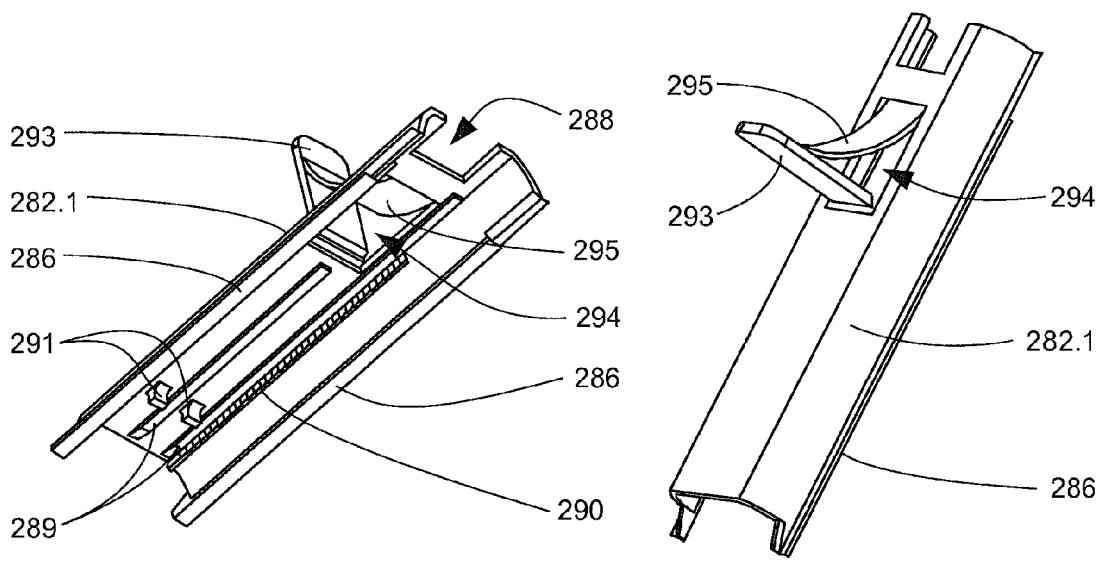
Figure 9C:
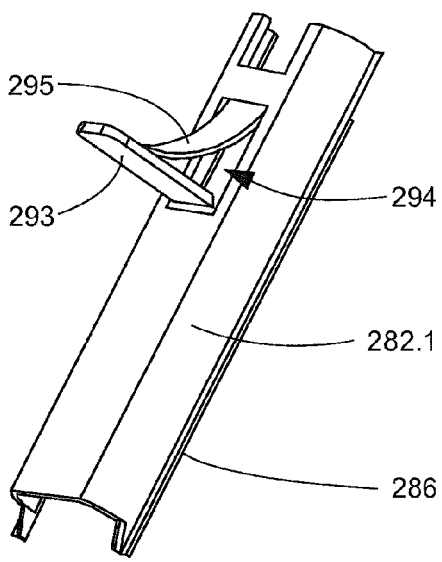
FIG. 9c shows an outer oblique view of an outer side of the housing part of FIG. 9b.

The dispensing device 280 comprises a housing 282 with two shell-shaped housing parts 282.1 and 282.2. In the present case, the two housing parts 282.1 and 282.2 are of substantially identical design. Only one of the housing parts 282.1 is therefore described in detail below. FIG. 9b shows an outer oblique view of an inner side of the housing part 282.1 and FIG. 9c shows an outer oblique view of an outer side of the housing part 282.1. FIGS. 9a-9c are jointly described below. It goes without saying that the housing parts can also be formed differently, depending on the application.

Perpendicularly to a longitudinal direction N of the dispensing device 280, the housing part 282.1 has a substantially U-shaped cross section with diverging arms. Web-like flanges 286 are formed along the free longitudinal edges of the arms, said flanges being provided for the connection to the further housing part 282.2 or for the connection to a container of the device 101 according to the invention (see below). In the joined-together state, the housing parts 282.1 and 282.2 bound a receiving space 283 of the dispensing device 280, said receiving space being open on the end side at both ends. At a front longitudinal end on the dispensing side, there is a receiving region 287 in which the closure piece 2' of the device 101 according to the invention can be arranged. In this region, an outer wall of the housing part 282.1 has a recess 288 through which the closure piece 2' or a connecting cap 50' attached thereto is accessible, for example, for the pinching-off of the rib 32' or for the manipulation of the closure means 56' and 57'. The flanges 286 are interrupted in the region of the receiving region 287, and therefore the edges 8' and 9' of the closure piece 2' are arrangable and fastenable between the housing parts 282.1 and 282.2.

On the inner side, the housing part 282.1 has guide rails 289 for a plunger 284 which can be pushed from an actuating end into the receiving space 283. On the inner side, there are latching rails 290 with a toothing in which correspondingly designed latching hooks of the plunger 284 engage. The plunger 284 can therefore be pushed stepwise along the guide rails 289 into the receiving space, but cannot be pulled back again. It goes without saying that, depending on the application, the latching rail does not need to be provided.

In order to prevent the plunger 284 from being completely pulled out prior to a first actuation, the inner side of the housing part 282.1 has two retaining projections 291. The latter project into corresponding longitudinal grooves 292 of the plunger 284, said longitudinal grooves being closed off at a front end. The plunger 284 therefore cannot be pulled back when the projections 291 strike against the ends of the grooves 292.

In a front region, behind the recess 288, the housing part 282.1 has an unfoldable finger flange 293. The finger flange 293 is articulated at a rear end of a recess 294 of the outer wall of the housing part 282.1 so as to be unfoldable about a transverse axis. As an example of a joint, a film joint formed as a single piece with the housing part 282.1 and the finger flange 293 can be used. The finger flange 293 is supported at a front end of the recess 294 via a flexible spring tongue 295, which can likewise be formed as a single piece with the housing part 282.1 and the finger flange 295. In the folded-in state (see FIGS. 9d-9e), the finger flange 293 and the folded spring tongue 295 are at least partially arranged in the recess 294. In the operationally ready state, the finger flange 293 is unfolded rearward and brought into a position oriented substantially perpendicularly to the longitudinal axis N. In the unfolded state, the spring tongue 293 prevents the finger flange 293 from being able to be folded further rearward. The finger flange 293 therefore serves as a counter support for the fingers of a user in the manner of a conventional syringe.

A container 138 of the device 101 can advantageously be fastened, for example welded, at the longitudinal borders 296 thereof between the flanges 286 of the housing parts 282.1 and 282.2. The container 138 is preferably fastened to the housing parts 282.1 and 282.2 prior to filling. This ensures that a deformation of the container 138 occurring at most during the filling is reduced. A further function of the supporting structure consists in that the device 101 can thereby be introduced in a simple and reproducible manner into a further device, for example for the automatic removal of the contents, or can be mounted in said device. In this case, the housing 282 acts as a structural support of the container 138. Alternatively, a frame which acts as a supporting structure for the container 138 can also be integrally formed, for example, on the closure piece 2'.

Figures 9D, 9E:
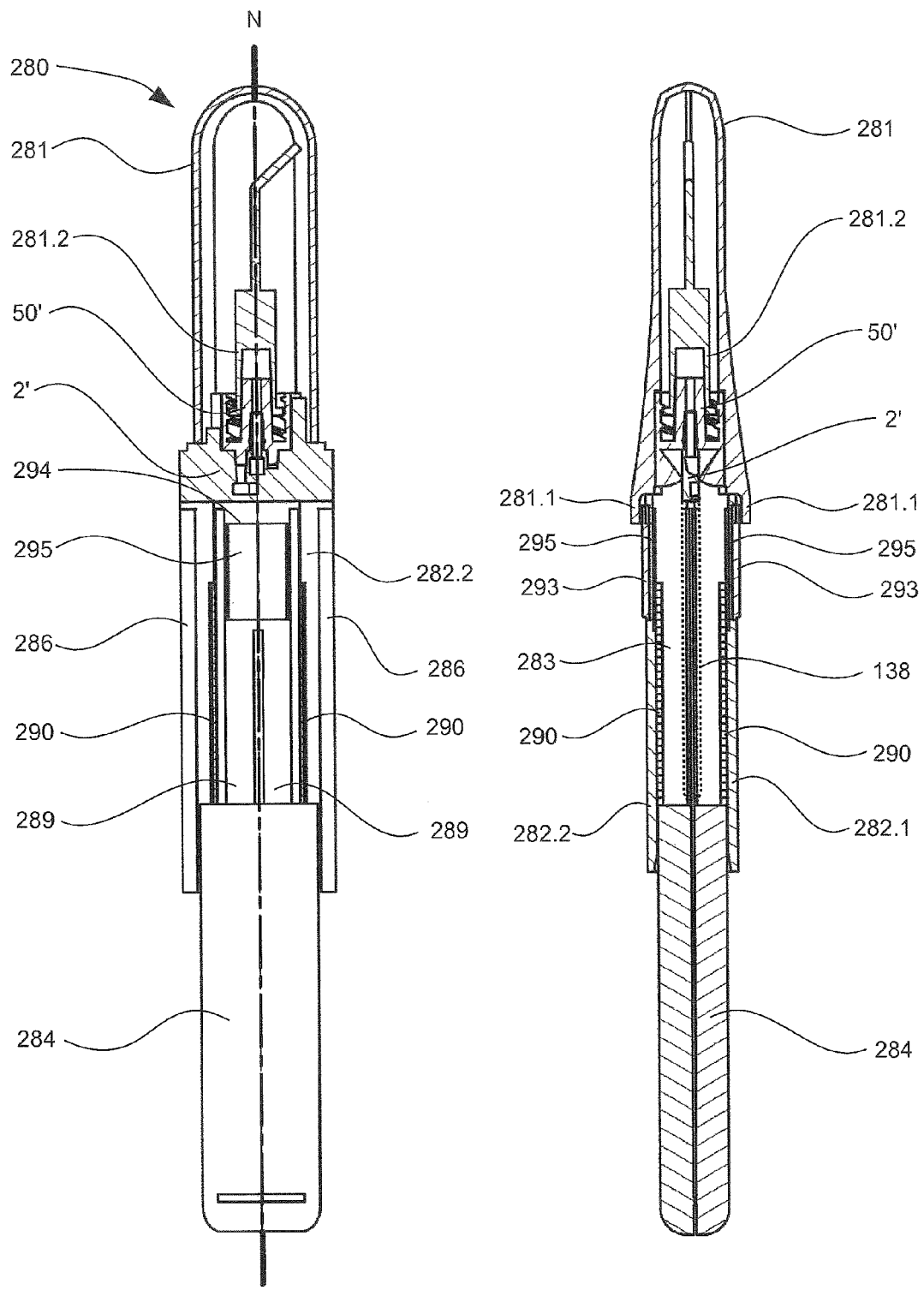
FIG. 9d shows a sectional view of the dispensing device of FIG. 9a in a center plane.
FIG. 9e shows a sectional view of the dispensing device of FIG. 9a in a center plane perpendicular to the sectional plane of FIG. 9d.

FIGS. 9d and 9e show the dispensing device 280 with an attached closure cap 281 in a transport or storage state (analogously to FIG. 3b). The closure cap 281 here has holding means 281.1 which partially engage over the folded-in finger flanges 293 and hold the latter in the folded-in state. The finger flanges 293 can therefore be unfolded only after the closure cap 281 is removed. In the interior of the closure cap 281, there is a closure means 281.2 which, in the attached state, is pulled over a cone of the connecting cap 50' and closes a dispensing opening.

Figure 10:
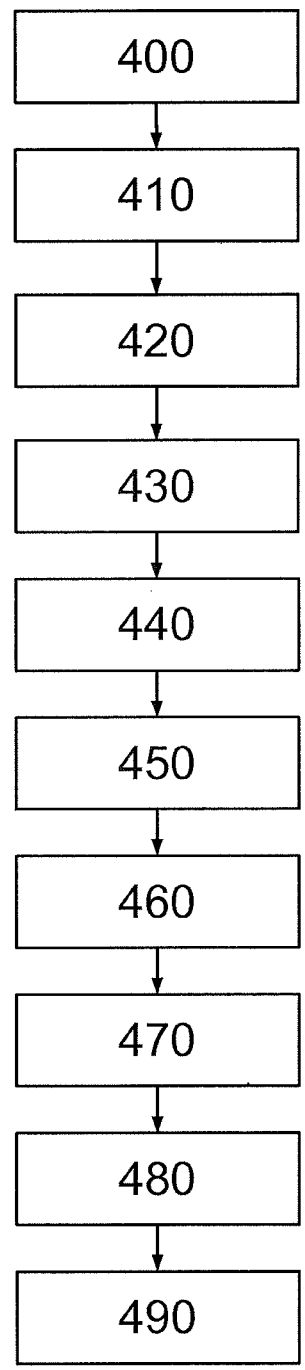
FIG. 10 shows a flow diagram of a method for filling a device according to the invention.

FIG. 10 shows a flow diagram of a method for filling a device according to the invention. A filling device with a filling needle for introduction into the connecting opening 30 or 30' of a closure piece 2 or 2' can be used here.

In a first step 400, the device is positioned in a desired filling position. In a further step 410, the valve device 23 or 23' is blocked, for example by the flexible membrane being squeezed off at the web 26 or 26'. After the filling needle has been introduced into the connecting opening 30 or 30' in a step 420, the fluid 39 can be introduced in a metered manner into the container 38 or 138 in a step 430. In a subsequent step 440, the removal opening 21 or 21' is closed, for example, by squeezing off the flexible membrane from the outside against the rib 32 or 32'. An interior space in the container is therefore closed off and, in a step 450, the filling needle can be removed from the connecting opening 30 or 30'. The valve device 23 or 23' can subsequently be released (step 460), for example by the flexible membrane no longer being pressed from the outside against the web 26 or 26'. After the closure piece 2 or 2' is closed with a connecting cap 50 or 50' and/or with other closure means (step 470), the removal opening can also be released, for example at the rib 32 or 32' (step 480). The device 1 or 101 which is therefore filled and closed can then be removed, for example, from the filling device and, for example, supplied for use or, if required, the dispensing device can be fitted (step 490).

The device according to the invention for receiving and dispensing a fluid therefore provides diverse possibilities for use, and can be used in a very wide variety of fields, in particular in connection with the connecting cap, which can be designed substantially as desired.

The invention claimed is:

1. A device for receiving or dispensing a fluid comprising a container and a closure piece, the closure piece comprising:

a) a connecting region for connection of the container, wherein a removal opening is arranged in the connecting region in such a manner that said removal opening communicates with an interior space in the container, and b) a dispensing region in which, in order to dispense the fluid, a dispensing opening is formed, and c) a dispensing channel which connects the dispensing opening fluidically to the removal opening, wherein a dispensing section of the dispensing channel communicates with the dispensing opening and a removal section of the dispensing channel communicates with the removal opening, d) wherein the dispensing channel comprises a valve device which, in a closed position, closes the dispensing channel in a fluid-tight manner and, in an open position, permits passage of the fluid through the dispensing channel if there is a positive pressure of sufficient size in a fluid in the removal section, and wherein the valve device has two valve openings which are arranged next to each other on a valve surface and of which a first valve opening communicates with the dispensing opening via the dispensing section of the dispensing channel and a second valve opening communicates with the removal opening via the removal section of the dispensing channel, and there is a continuous, flexible membrane which, in the closed position of the valve device, bears against the valve surface so as to be raisable in regions and thus closes off the valve openings from each other in a fluid-tight manner, a container wall of the container is designed so as to be flexible at least in regions and, in the connecting region, the closure piece has at least one connecting surface to which a connecting section of the container wall is fastened, and the connecting section of the container wall is designed so as to be flexible, and the valve surface with valve openings is arranged on the at least one connecting surface of the closure piece in such a manner that a region of the connecting section of the container wall forms the flexible membrane of the valve device.

2. The device as claimed in claim 1, wherein, in the connecting region, the closure piece has a section of cylindrical design and the at least one connecting surface is formed on an outer lateral area of the cylindrical section.

3. The device as claimed in claim 2, wherein, in addition to the at least one connecting surface, the lateral area of the cylindrical section comprises a further connecting surface, wherein the two connecting surfaces converge pairwise at a common edge and therefore the cylindrical section has a lenticular base surface.

4. The device as claimed in claim 1, wherein a coupling element for the direct or indirect coupling of the device to a fluid-conducting component is formed on the closure piece in the dispensing region, which coupling element has a fluid channel which is connected to the dispensing opening.

5. The device as claimed in claim 2, wherein there is a connecting cap which is attachable to the closure piece and closes the connecting opening in the dispensing region of the closure piece.

6. The device as claimed in claim 5, wherein the connecting cap has a coupling means for the fluid-communicating coupling of the dispensing opening to a fluid-conducting system.

7. The device as claimed in claim 5, wherein the connecting cap has a receiving space which is of complementary design to the coupling element of the closure piece and in which the coupling element is receivable when the connecting cap is attached.

8. The device as claimed in claim 5, wherein the connecting cap has a closure means which is designed in such a manner that, when the connecting cap is attached, said closure means fixes the valve device in the closed position.

9. The device as claimed in claim 8, wherein the closure means is designed and arranged in such a manner that the flexible membrane is fixedly pressable onto the valve surface by the closure means in the region between the valve openings.

10. The device as claimed in claim 1, wherein there is a supporting structure to which the container is fixedly connected.

11. The device as claimed in claim 10, wherein the supporting structure is provided by a dispensing device with a receiving space which is bounded by a housing and in which the container is arranged, and wherein the container is fixedly connected to the housing.

12. A device for receiving or dispensing a fluid comprising a container and a closure piece, and the closure piece comprising:

a) connecting region for connection of the container, and a removal opening is arranged in the connecting region in such a manner that said removal opening communicates with an interior space in the container, b) a dispensing region in which, in order to dispense the fluid, a dispensing opening is formed, c) a dispensing channel which connects the dispensing opening fluidically to the removal opening, and a dispensing section of the dispensing channel communicates with the dispensing opening and a removal section of the dispensing channel communicates with the removal opening, d) the dispensing channel comprises a valve device which, in a closed position, closes the dispensing channel in a fluid-tight manner and, in an open position, permits passage of the fluid through the dispensing channel if there is a positive pressure of sufficient size in a fluid in the removal section, the valve device has two valve openings which are arranged next to each other on a valve surface and of which a first valve opening communicates with the dispensing opening, via the dispensing section of the dispensing channel, and a second value opening communicates with the removal opening, via the removal section of the dispensing channel, and there is a continuous, flexible membrane which, in the closed position of the valve device, bears against the valve surface so as to be raisable in regions and thus closes off the valve openings from each other in a fluid-tight manner, and the closure piece comprises a filling channel for filling the container, said filling channel fluidically connecting a connecting opening for connecting a fluid source in the dispensing region and a filling opening in the connecting region, said filling opening communicating with the interior space in the container.

13. A method for filling a device for receiving or dispensing a fluid by means of a filling device, the device for receiving or dispensing the fluid comprising a container and a closure piece, the closure piece comprising:

a) a connecting region for connection of the container, and a removal opening is arranged in the connecting region in such a manner that said removal opening communicates with an interior space in the container, b) a dispensing region in which, in order to dispense the fluid, a dispensing opening is formed,
c) a dispensing channel which connects the dispensing opening fluidically to the removal opening, and a dispensing section of the dispensing channel communicates with the dispensing opening and a removal section of the dispensing channel communicates with the removal opening,
d) the dispensing channel comprises a valve device which, in a closed position closes the dispensing channel in a fluid-tight manner and, in an open position, permits passage of the fluid through the dispensing channel if there is a positive pressure of sufficient size in a fluid in the removal section,
the valve device has two valve openings which are arranged next to each other on a valve surface and of which a first valve opening communicates with the dispensing opening, via the dispensing section of the dispensing channel, and a second valve opening communicates with the removal opening, via the removal section of the dispensing channel, and there is a continuous, flexible membrane which, in the closed position of the valve device, bears against the valve surface so as to be raisable in regions and thus closes off the valve openings from each other in a fluid-tight manner, the method comprising the follow steps:
a) coupling the filling device to the dispensing channel of the closure piece of the device,
b) feeding a fluid from the filling device through the dispensing channel into the container,
c) closing of the removal opening in relation to the interior space in the container,
d) decoupling the filling device,
e) closing the closure piece with a closure cap, and
f) releasing the removal opening.

* * * * *